US012714342B2

(12) United States Patent
Ihlefeld et al.

(10) Patent No.: US 12,714,342 B2
(45) Date of Patent: Aug. 25, 2026

(54) IN-EAR FUNCTIONAL NEAR-INFRARED SPECTROSCOPY FOR COGNITIVE LOAD ESTIMATION

(71) Applicant: META PLATFORMS TECHNOLOGIES, LLC, Menlo Park, CA (US)

(72) Inventors: Antje Ihlefeld, Redmond, WA (US); Morteza Khaleghimeybodi, Bothell, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 997 days.

(21) Appl. No.: 17/752,284

(22) Filed: May 24, 2022

(65) Prior Publication Data

US 2023/0380739 A1 Nov. 30, 2023

(51) Int. Cl.

| | |
|---|---|
| ***A61B 5/16*** | (2006.01) |
| ***A61B 5/00*** | (2006.01) |
| ***A61B 5/291*** | (2021.01) |
| ***A61B 5/369*** | (2021.01) |
| ***H04R 1/10*** | (2006.01) |

(52) U.S. Cl.

CPC .............. *A61B 5/16* (2013.01); *A61B 5/0075* (2013.01); *A61B 5/0082* (2013.01); *A61B 5/291* (2021.01); *A61B 5/369* (2021.01); *A61B 5/6803* (2013.01); *A61B 5/7225* (2013.01); *H04R 1/1016* (2013.01); *H04R 1/1041* (2013.01)

(58) Field of Classification Search
None
See application file for complete search history.

(56) References Cited

U.S. PATENT DOCUMENTS 10,901,509 B2 1/2021 Aimone et al.
2018/0348863 A1* 12/2018 Aimone .................. G06F 3/011
2019/0107888 A1* 4/2019 Sereshkeh .............. A61B 5/374
2019/0321655 A1* 10/2019 Riis ...................... A61B 5/0017

OTHER PUBLICATIONS

Rovetti, Joseph, et al., Functional Near-Infrared Spectroscopy as a Measure of Listening Effort in Older Adults Who Use Hearing Aids, Sep. 2019, Sage Pub, vol. 23, 1-22 (Year: 2019).*

(Continued)

*Primary Examiner* — Aurelie H Tu
(74) *Attorney, Agent, or Firm* — Greenberg Traurig, LLP

(57) ABSTRACT

A cognitive load estimation system. The system includes an-in ear device (IED) configured to be placed within an ear canal of a user. The IED includes a first set of functional near-infrared spectroscopy (fNIRS) optodes that are configured to capture first fNIRS signal data representing hemodynamic changes in a brain of the user. The system further includes at least one electroencephalography (EEG) electrode configured to capture electrical signals corresponding to brain activity of the user. The system further includes a controller configured to filter the first fNIRS signal data based in part on the electrical signals to generate filtered fNIRS signal data. The controller is further configured to estimate a cognitive load of the user based on the filtered fNIRS signal data.

20 Claims, 6 Drawing Sheets

(56) References Cited

OTHER PUBLICATIONS

Karmakar, Subashis, et al., Real time detection of cognitive load using fNIRS: A deep learning approach, Oct. 2022, Biomedical Signal Processing and Control, vol. 80 (Year: 2022).*
Bell, Laura, et al., fNIRS Assessment of Speech Comprehension in Children with Normal Hearing and Children with Hearing Aids in Virtual Acoustic Environments: Pilot Data and Practical Recommendations, Sep. 2020, Children, vol. 7, 1-25 (Year: 2020).*
Vaisberg, Jonathan, et al., The Benefit of Hearing Aids as Measured by Listening Accuracy, Subjective Listening Effort, and Functional Near Infrared Spectroscopy, Jul. 2024, Sage, vol. 28, 1-19 (Year: 2024).*
BU Neurophotonics Center, "Neuroimaging in the Everyday World," Aug. 20, 2021, 13 pages, Retrieved from the Internet: URL: https://www.bu.edu/neurophotonics/2021/08/20/neuroimaging-in-the-everyday-world/.
GTEC, "Sensor FNIRS: 8 FNIRS Channels Add-On," 2021, 7 pages, Retrieved from the Internet: URL: https://www.gtec.at/product/fnirs-sensor/.
Pfeifer M.D., et al., "Signal Processing in Functional Near-Infrared Spectroscopy (fNIRS): Methodological Differences Lead to Different Statistical Results," Frontiers in Human Neuroscience, vol. 11, Article 641, Jan. 8, 2018, 12 pages.
Piquado T., et al., "Pupillometry as a Measure of Cognitive Effort in Younger and Older Adults," Psychophysiology, vol. 47, No. 3, May 1, 2010, 18 pages.
Plux Wireless Biosignals S.A., "FNIRS Explorer," Ref: 820202411, UPC Barcode: 785614264771, 2021, 3 pages.
Uchitel J., et al., "Wearable, Integrated EEG-fNIRS Technologies: A Review," Sensors, vol. 21, 2021, 19 pages.
Zhang M., et al., "Hemodynamic Responses Link Individual Differences in Informational Masking to the Vicinity of Superior Temporal Gyrus," Frontiers in Neuroscience, vol. 15, Article 675326, Jul. 22, 2021, 14 pages.

* cited by examiner

IN-EAR FUNCTIONAL NEAR-INFRARED SPECTROSCOPY FOR COGNITIVE LOAD ESTIMATION

FIELD OF THE INVENTION

The present disclosure generally relates to functional near-infrared spectroscopy (fNIRS), and specifically relates to in-ear fNIRS for cognitive load estimation.

BACKGROUND

Functional near-infrared spectroscopy is an optical brain imaging technique that estimates hemodynamic changes in the brain's cortex by shining light (e.g., light emitting diode (LED) light, laser light, etc.) into the head of the user and comparing light absorption across different wavelengths via the Beer-Lambert law principle. Unlike other tissue in the head, in neural tissue, hemodynamic changes in oxygenated hemoglobin (HbO) and deoxygenated hemoglobin (HbR) are constrained to be anti-correlated across time. Thus, fNIRS can be used to estimate the responsiveness of neural brain tissue from HbO and/or HbR traces. That is, since the oxygenation level changes as brain areas become more active, brain activity can be identified in real-time by detecting the changes in blood oxygenation using an fNIRS device. Conventional fNIRS devices identify brain activity by accessing the cortex from the surface of the skull via optodes (e.g., sensors and detectors) that are strapped around the head or mounted via a headcap. However, such conventional systems are bulky, and not suitable for use in a portable, wearable device setting.

SUMMARY

Embodiments include a cognitive load estimation system that includes an in-ear device (IED) that is configured to capture fNIRS signals (e.g., fNIRS signal data) using at least one set (e.g., one pair) of fNIRS optodes disposed on the IED The system may further include an EEG electrode to capture electrical signals (e.g., EEG signal data) that represent brain activity of the user. The system may then utilize the EEG signal data to filter the fNIRS signal data to separate out neural signals representing brain activity from noise. The IED device may further include a second set of fNIRS optodes that are reciprocal to the at least one set, so as to capture reciprocal fNIRS signal data (e.g., bidirectional signal capture) that can also be used to detect and correct for measurement errors by filtering the fNIRS signal data based on the reciprocal data. The system may further include a headset, and an additional fNIRS optode set may be disposed in the headset to generate additional fNIRS signal data.

In one embodiment, a system is provided which includes an-in ear device (IED) configured to be placed within an ear canal of a user. The IED includes a first set of functional near-infrared spectroscopy (fNIRS) optodes that are configured to capture first fNIRS signal data representing hemodynamic changes in a brain of the user. The system further includes at least one electroencephalography (EEG) electrode configured to generate electrical signals corresponding to brain activity of the user. The system further includes a controller configured to filter the first fNIRS signal data based in part on the electrical signals to generate filtered fNIRS signal data. The controller is further configured to estimate a cognitive load of the user based on the filtered fNIRS signal data.

In another embodiment, an in-ear device (IED) is provided which is configured to be placed within an ear canal of a user. The IED includes a first set of functional near-infrared spectroscopy (fNIRS) optodes that are configured to capture first fNIRS signal data representing hemodynamic changes in a brain of the user. The IED further includes at least one electroencephalography (EEG) electrode that is disposed on the IED so as to be in contact with an inner surface of the ear canal, and that is configured to capture electrical signals corresponding to brain activity of the user. The IED further includes a controller configured to filter the first fNIRS signal data based in part on the electrical signals to generate filtered fNIRS signal data. The controller is further configured to estimate a cognitive load of the user based on the filtered fNIRS signal data. Alternately, or in addition, the controller may be configured to estimate the cognitive load of the user based on the EEG signal data. In some embodiments, the controller may be configured to combine the filtered fNIRS signal data and the EEG signal data to generate combined signal data, and estimate the cognitive load based on the combined signal data.

In yet another embodiment, a method is provided which comprises the step of capturing first fNIRS signal data with a first set of functional near-infrared spectroscopy (fNIRS) optodes disposed on an in-ear device (IED) configured to be placed within an ear canal of a user. The first fNIRS signal data represents hemodynamic changes in a brain of the user. The method further includes the steps of capturing electrical signals corresponding to brain's activity of the user, and filtering the first fNIRS signal data based in part on the electrical signals to generate filtered fNIRS signal data. The method further includes the step of estimating a cognitive load of the user based on the filtered fNIRS signal data.

Figures 1, 2A, 2B, 2C:
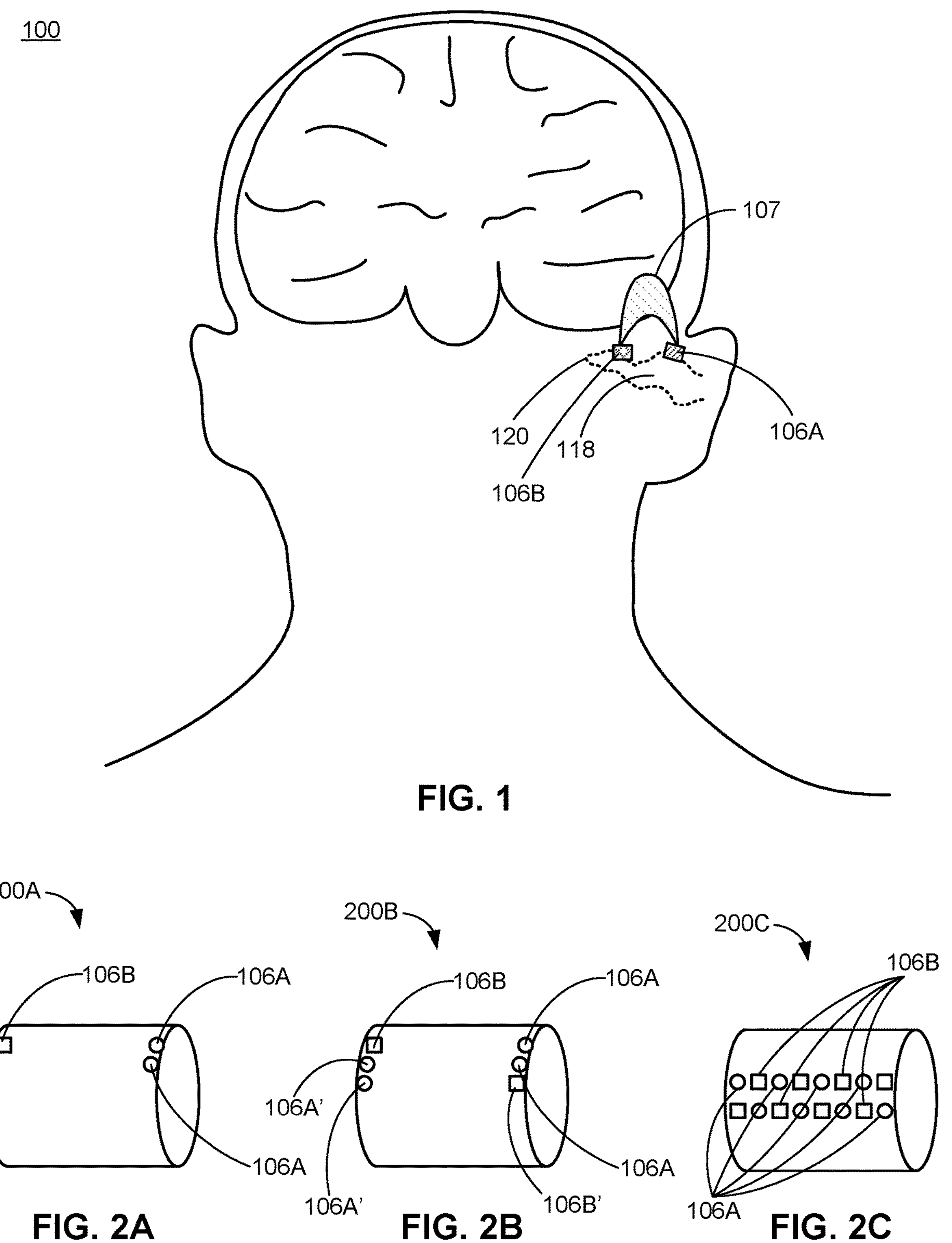
FIG. 1 is a schematic diagram illustrating a technique for in-ear fNIRS signal data measurement, in accordance with one or more embodiments.
FIGS. 2A-2C are perspective, schematic views showing different exemplary configurations of fNIRS optode sets embedded in an IED, in accordance with one or more embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

This disclosure pertains to an in-ear based cognitive load estimation system (e.g., fNIRS system), in-ear device (IED), and corresponding method. The system may include one or more of the IEDs, and may also include a headset (e.g., eyeglasses, over ear headphones, head mounted display, headphones). The system may further include a sensor device (e.g., including optodes/electrodes mounted to the scalp via a strap or headcap) that is separate from the IEDs and the headset. The one or more IEDs may each include one or more sets (e.g., pairs) of fNIRS optodes, each set including one or more light sources emitting light and one or more detectors, that respectively generate fNIRS signal data. The fNIRS optode sets may be used to capture fNIRS signal data representing hemodynamic changes in a brain of the user. In some embodiments, the fNIRS optode sets may include a reciprocal set of fNIRS optodes to capture the fNIRS signals reciprocally (e.g., bidirectionally), as opposed to unidirectionally, and correct for measurement errors by comparing the bidirectional fNIRS signal data and subtracting noise from true neural signal.

In some embodiments, the system may further include one or more electrodes for measuring electrical signals of the brain (e.g., electric field potentials of many neurons in the brain firing simultaneously; EEG signal data) to correct the fNIRS signal data by filtering out signals having a systemic origin from the fNIRS signals having a neural origin and representing true brain activity. The one or more electrodes may be included in the headset, in the IEDs, in the sensor device, or some combination thereof.

The system may further include additional fNIRS optode sets (e.g., in addition to the reciprocal sets) including one or more sources and one or more detectors for capturing additional fNIRS signal data that may be used to further filter out noise or to obtain additional brain activity information. The additional fNIRS optode sets may be included in the headset, in the IEDs, in the sensor device, or some combination thereof. The EEG signal data, the fNIRS signal data from the reciprocal set, the additional fNIRS signal data from the additional optode set(s), or some combination thereof, may be used to filter the (original, unfiltered) fNIRS signal data from the original set of fNIRS optodes disposed on the IED to generate filtered fNIRS signal data. The filtered fNIRS signal data may be used to estimate (measure) a cognitive load (e.g., listening effort, listener's intent, and the like) of the user. The filtration of the fNIRS signal data may mitigate any error in the cognitive load estimation.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to create content in an artificial reality and/or are otherwise used in an artificial reality. The artificial reality system that provides the artificial reality content may be implemented on various platforms, including a wearable device (e.g., headset) connected to a host computer system, a standalone wearable device (e.g., headset), a mobile device or computing system, or any other hardware platform capable of providing artificial reality content to one or more viewers.

FIG. 1 is a schematic diagram 100 illustrating a technique for in-ear fNIRS signal data measurement, in accordance with one or more embodiments. The schematic diagram 100 illustrates a set (e.g., pair) of fNIRS optodes 106 of an in-ear fNIRS device (not shown in FIG. 1) disposed within an ear canal 118 of a user near an eardrum 120 of the user. As used herein, a set of fNIRS optodes 106 may include at least one source optode 106A and at least one detector optode 106B, that can be used to generate fNIRS signal data.

fNIRS is an optical brain imaging technique that estimates hemodynamic changes in the brain's cortex by shining light (from, e.g., a light emitting diode (LED), a laser, etc.) into the head of the user, and comparing light absorption across different wavelengths via the Beer-Lambert law principle. Unlike other tissue in the head, in neural tissue, hemodynamic changes in hemoglobin oxygenation (HbO) and hemoglobin deoxygenation (HbR) are constrained to be anti-correlated across time. Thus, since the oxygenation level changes as brain areas become more active, brain activity can be identified and monitored in real-time by detecting the changes in blood oxygenation represented by the HbO and/or HbR traces using an fNIRS device that includes a set of fNIRS optodes.

When a user listens for sound in crowded environments, the background sound can make it difficult for the user to understand what people around the user are saying. The brain activity identified and monitored in real-time by the fNIRS device can be used to estimate both what the user is trying to hear, and how much strain the user is experiencing in trying to hear what the user is focusing on (e.g., estimate how much difficulty the person experiences, estimate the cognitive load, estimate the listening effort, estimate listener's intent, and the like).

An fNIRS device can be applied to cortical regions of the brain that are more engaged with active listening as compared to a situation where a person passively hears sound. More specifically, the fNIRS device can be applied to a portion of the temporal lobe of the brain called superior temporal gyms (STG; see FIG. 1) as well as portions of frontal cortex that are recruited for active listening. That is, cognitive load is thought to be related to the amount of blood oxygenation change in the STG. One way to access this signal is through fNIRS, that detects how much blood oxygenation changes as light is shined through the skull. Thus, an fNIRS device can be applied to measure activations near the STG that correlate with a listener's vulnerability to background sound and likely attributable to cognitive load (e.g., listening effort, listening fatigue), as opposed to just the percentage of words the listener can correctly understand (or not understand) despite being able to hear the words clearly.

Conventional fNIRS devices access the cortex from the surface of the scalp, via optodes (e.g., sources, detectors) that must be strapped around the head or mounted via a headcap. Such conventional fNIRS devices have several disadvantages. First, the conventional fNIRS devices tend to be bulky, and not fit for use in a portable, minimalist, wearable device setting. Second, mounting the optodes on the surface of the head disadvantages users with coarse hair or hair that is tightly braided, because the optodes cannot get close enough to the skull to be able to capture accurate fNIRS signal data. Third, the conventional fNIRS devices need to be strapped tightly, to minimize leakage light from the optodes, and therefore usually become uncomfortable after 30-60 minutes of use.

To overcome the above problems, as shown in FIG. 1, the present disclosure proposes an in-ear based fNIRS measurement technique that can achieve continuous, unobtrusive monitoring of the cognitive load by using a wearable in-ear fNIRS device (see, e.g., as described in detail below in connection with FIGS. 2-3) that includes at least one set of fNIRS optodes 106, that leverages the anatomy of the ear canal 118 to record from the temporal lobe that is ipsilateral to device placement (e.g., a set of fNIRS optodes 106 in the IED for the left ear records from the left STG), that utilizes the ear canal 118 to stably position the set of fNIRS optodes 106 and minimize light leakage, and that is embedded in an earplug to enable comfortable long-term recordings of fNIRS signal data and corresponding monitoring of the user's cognitive load.

As shown in FIG. 1, the source optode 106A and the detector optode 106B of the set of FNIRS optodes 106 define a curved optical path 107 that may capture brain activity from inside the ear canal 118. The light travels along the curved optical path 107, from the source optode 106A (e.g., light emitter) through the scalp, then through the skull, and into the brain tissue of the user. The light then travels back through the skull and the scalp to the detector optode 106B. Absorption of this light at the detector optode 106B can be used to estimate HbO and HbR, which in turn allows estimation of neural activity in the brain.

More specifically, according to the Beer-Lambert law principle, HbO and HbR absorb light differently as a function of wavelength. As light passes thorough the tissues, the saturated and desaturated hemoglobin absorbs different frequencies of light. For example, fully desaturated hemoglobin absorbs red lights (e.g., 630 nm), and fully saturated hemoglobin absorbs infrared light (e.g., 940 nm). Measuring light absorption at two or more wavelengths can therefore be leveraged to estimate HbO and HbR concentrations. And based on the estimated HbO and HbR concentrations, neural activity in the brain can be estimated as the (unfiltered) fNIRS signal data.

The spacing between the source optode 106A and the detector optode 106B of the set controls the recording depth. That is, the further the source optode 106A is spaced apart from the detector optode 106B, the deeper the penetration of the curved optical path 107 into the brain tissue is, and the deeper the recording depth is. By contrast, the further the source optode 106A is spaced apart from the detector optode 106B, the poorer the signal quality of the fNIRS signal captured at the detector optode 106B becomes, due to more light getting scattered along the optical path. In some embodiments, a distance between the source optode 106A and the detector optode 106B (source detector separation (SDS)) of the set may be at least a predetermined distance. In some embodiments, to achieve a greater penetration depth, the SDS of the set may be at least 1 cm and preferably around 2.5 cm.

Each source optode 106A may be a near-infrared (NIR) light source that is configured to emit NIR light. For example, the source optode 106A may be a light emitting diode (LED). As another example, the source optode 106A may be a laser light source. Each source optode 106A may be configured to emit light at one or more predetermined wavelengths in a NIR range (e.g., between ~650 nm and ~1000 nm). For example, the source optode 106A may emit light at a first wavelength that may fall within a range of ~650 nm to ~780 nm. More specifically, the first wavelength may fall within a range of ~670 nm to ~730 nm. Even more specifically, the first wavelength may fall within a range of ~680 nm to ~710 nm. As a concrete example, the first wavelength may be 695 nm. In addition, or in the alternative, the source optode 106A may emit light at a second wavelength that may fall within a range of ~810 nm to ~1000 nm. More specifically, the second wavelength may fall within a range of ~820 nm to ~900 nm. Even more specifically, the second wavelength may fall within a range of ~830 nm to ~900 nm. As a concrete example, the second wavelength may be 830 nm. In some embodiments, the first and second wavelengths are chosen to maximize the differentiation in the absorption of the deoxy- vs oxy-hemoglobin (e.g., 700 and 900 nm, respectively).

Each of the detector optodes 106B may be a NIR light detector configured to detect NIR light. For example, the detector optode 106B may be a photodetector. Each of the detector optodes 106B may be configured to detect light at one or more predetermined wavelengths in the NIR range (e.g., between ~650 nm and ~1000 nm). For example, the detector optode 106B may be configured to detect light at the first wavelength. In addition, or in the alternative, the detector optode 106B may be configured to detect light at the second wavelength.

FIGS. 2A-2C are perspective, schematic views showing different exemplary configurations of fNIRS optode sets embedded in an IED 200 (e.g., IED 200A in FIG. 2A, IED 200B in FIG. 2B, IED 200C in FIG. 2C). For the sake of simplicity, components of the IED 200 other than the fNIRS optode sets are not shown in FIGS. 2A-2C. As shown in FIGS. 2A-2C, at least one set of fNIRS optodes 106 is disposed on the IED 200A-C, the set including at least one source (e.g., emitter) optode 106A and at least one detector optode 106B, that operate to generate the (unfiltered) fNIRS signal data for the set.

Figure 3:
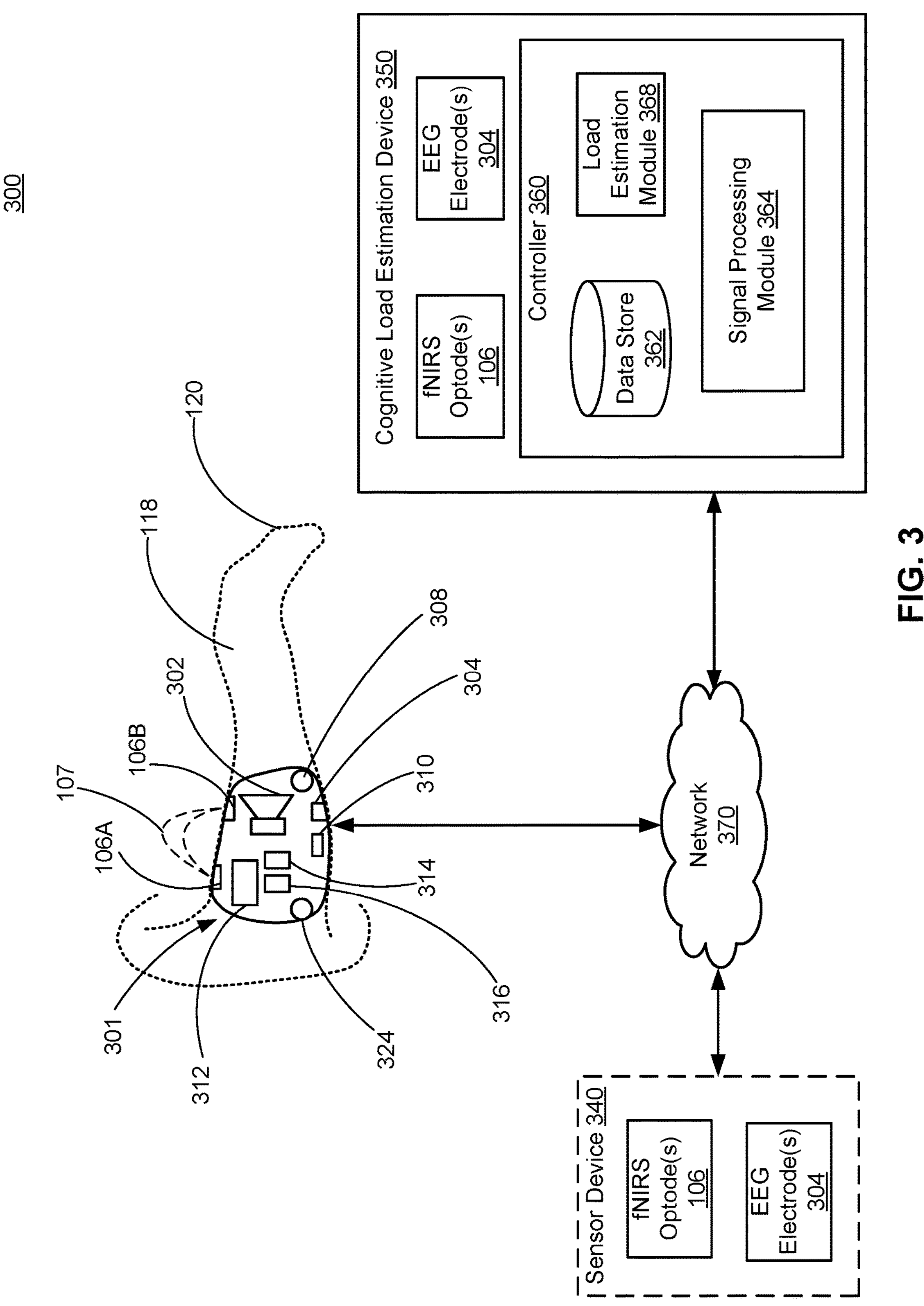
FIG. 3 is a block diagram of a cognitive load estimation system, in accordance with one or more embodiments.

As shown in FIG. 2A, the IED 200A may include one set of fNIRS optodes 106. The set may include two source optodes 106A, and one detector optode 106B. The IED 200A may record the fNIRS signal data unilaterally. That is, the IED 200A may record the fNIRS signal data based on the curved optical path that extends from the source optodes 106A to the detector optode 106B. The source optodes 106A are configured to respectively emit two different wavelengths of NIR light (e.g., the first and second wavelengths), and the detector optode 106B is configured to detect both of the wavelengths of NIR light. In another embodiment, the IED 200 (e.g., as shown in FIG. 3) may include one set of fNIRS optodes 106 including one source optode 106A and one detector optode 106B. The source optode 106A is configured to generate one or more wavelengths of NIR light, and the detector optode 106B is configured to detect the one or more wavelengths of NIR light.

In the example configuration of FIG. 2A, the source optodes 106A may be time-multiplexed and time-synchronized with the detector optode 106B. That is, the source optodes 106A may be powered on in sequence (e.g., 1-2 milliseconds at-a-time for each optode 106A) to emit the two different wavelengths (or in case there is one source optode, the same source optode controlled to emit the two different wavelengths in sequence), and the detector optode may be time-synchronized and configured to detect the corresponding wavelength light. The detected light may be used to generate the (unfiltered) fNIRS signal data for the set. In other embodiments, the source optodes 106A and the detector optode 106B may be spectrally multiplexed (i.e., via wavelength diffraction) and be time-synchronized. That is, the two source optodes 106A may be powered on simultaneously to emit the two different wavelengths at the same time (or in case there is one source optode, the same optode controlled to emit the two different wavelengths simultaneously), and the detector optode 106B may be time-synchronized and configured to detect the two different wavelengths at the same time, and then spectrally separate the fNIRS signals for the two different wavelengths to generate the (unfiltered) fNIRS signal data.

Further, as shown in FIG. 2B, in some embodiments, the fNIRS signal data may be recorded bidirectionally (e.g., reciprocally) instead of being recorded unilaterally (as is the case in FIG. 2A). To capture the fNIRS signal data bidirectionally, the IED 200B may be embedded with a reciprocal (e.g., second) set of fNIRS optodes 106' that is reciprocal to the other (e.g., first, original) set of fNIRS optodes 106. That is, the IED 200B of FIG. 2B includes a reciprocal set of fNIRS optodes 106' including the source optodes 106A' and the detector optode 106B'. The reciprocal set of fNIRS optodes 106' may be configured to capture reciprocal fNIRS signal data over substantially the same area (or proximate to the same area) as the fNIRS signal data recorded by the first set of fNIRS optodes 106. That is, the curved optical paths of the first set of fNIRS optodes 106 and the reciprocal set of fNIRS optodes 106' cover substantially the same area but have the light flowing in opposite directions through the area. The reciprocal set of fNIRS optodes 106' may be configured to capture the reciprocal fNIRS signal data time interleaved with the data captured by the (first) set of the fNIRS optodes 106 to increase a signal-to-noise ratio (SNR) of the captured fNIRS signal data. That is, by embedding the reciprocal set of fNIRS optodes 106', double feedback using the dual sets of optodes on each side of the in-ear module can be implemented to maximize the SNR.

More specifically, if light is transmitted from point A to point B using an fNIRS device, the curved optical path of such a transmission would be the substantially the same as (or proximate to) a curved optical path if the light were transmitted in the reciprocal path from point B to point A. Thus, the resulting (reciprocal) fNIRS signal data of the reciprocal path should be the same (or substantially the same for the purposes of this disclosure) as the (original) fNIRS signal data of the original curved optical path. To the extent that the fNIRS signal data of the reciprocal sets is different from each other, it may be possible to determine the reason for the disparity as being noise (as opposed to true brain activity signal), and it may be possible to denoise the original fNIRS signal data by using the difference information. For example, incorrect coupling of one or more of the optodes may cause the difference in the data recorded by the reciprocal sets, as extraneous noise is being picked up as the fNIRS signal when in fact the signal is unrelated to brain activity. As another example, the difference may be attributable to extraneous noise that is caused by systemic factors like body motion or motion of the optodes. Thus, by capturing the reciprocal fNIRS signal data, it may be possible to correct (e.g., denoise) for measurement errors in the original (first) fNIRS signal data (e.g., by using a controller in the TED 200B).

As explained above, the source optodes 106A and the detector optode 106B of the first set in the reciprocal sets may be time-multiplexed or spectrally multiplexed, and time-synchronized to generate the (original, unfiltered) fNIRS signal data. Similarly, the source optodes 106A' and the detector optode 106B' of the reciprocal set may also be time-multiplexed or spectrally multiplexed, and time-synchronized to generate the reciprocal fNIRS signal data. The reciprocal set may capture the reciprocal fNIRS signal data time interleaved with the fNIRS signal data captured by the first set of optodes 106.

That is, for example, operation of the source-detector sets of FIG. 2B may be time multiplexed to capture fNIRS signals in the following time sequential order: (1) The first set of fNIRS optodes 106—Wavelength 1; (2) The first set of fNIRS optodes 106—Wavelength 2; (3) The second (reciprocal) set of fNIRS optodes 106'—Wavelength 1; (4) The second set of fNIRS optodes 106'—Wavelength 2. As another example, operation of the source-detector sets of FIG. 2B may be time multiplexed to capture fNIRS signals in the following time sequential order: (1) The first set of fNIRS optodes 106—Wavelength 1; (2) The reciprocal set of fNIRS optodes 106'—Wavelength 1; (3) The first set of fNIRS optodes 106—Wavelength 2; (4) The reciprocal set of fNIRS optodes 106'—Wavelength 2. Further, for example, operation of the source-detector sets of FIG. 2B may be spectrally multiplexed to capture fNIRS signals in the following time sequential order: (1) The first set of fNIRS optodes 106—Wavelengths 1 & 2 (simultaneous capture and spectral separation); (2) The reciprocal set of fNIRS optodes 106'—Wavelengths 1 & 2 (simultaneous capture and spectral separation).

In some embodiments, more than two wavelengths may be emitted and captured to generate the original, unfiltered fNIRS signal data. The reciprocal fNIRS signal data of the reciprocal set of fNIRS optodes 106' may be generated using a lesser number of wavelengths than the number of wavelengths used for the original, unfiltered fNIRS signal data for the first set. For example, the original, unfiltered fNIRS signal data for the first set may be generated using two different wavelengths, while the reciprocal fNIRS signal data of the reciprocal set of fNIRS optodes 106' used for noise estimation may be generated using only one of the two different wavelengths.

In order to generate the reciprocal fNIRS signal data, as shown in FIG. 2B, the position of the source and detector optodes of the reciprocal set of fNIRS optodes 106' may be reciprocal to the positions of the source and detector optodes of the first set of fNIRS optodes 106. That is, the sets may be positioned so that the curved optical path of the first set of fNIRS optodes 106 may be substantially the same as the curved optical path of the reciprocal set of fNIRS optodes 106', while the direction of travel of the light from the source is reversed. Thus, for example, as shown in FIG. 2B, the detector optode 106B of the first set of fNIRS optodes 106 may be adjacent to the source optodes 106A' of the reciprocal set of fNIRS optodes 106', and the source optodes 106A of the first set of fNIRS optodes 106 may be adjacent the detector optode 106B' of the reciprocal set of fNIRS optodes 106'. Further, the source optodes 106A and the detector optode 106B' are disposed at one end of the IED 200B, and the detector optode 106B and the source optodes 106A' are disposed at the other end of the IED 200B, such that the SDS for the first set and the reciprocal set may be substantially the same. By including the reciprocal set of fNIRS optodes 106', the SNR of the fNIRS signal measurement can be enhanced. In order to be able to use the fNIRS signal data from the reciprocal set of fNIRS optodes 106' for enhancing the SNR of the fNIRS measurement, the SDS of the reciprocal set of fNIRS optodes 106' is substantially the same as the SDS of the first set of fNIRS optodes 106, so that both of both sets of optodes capture information from the same penetration depth (i.e., capture information from the same location within the brain's cortex).

Still further, as shown in FIG. 2C, in some embodiments, the IED 200C may include a plurality of sets of fNIRS optodes 106 (e.g., reciprocal set, and one or more additional sets) to generate the filtered fNIRS signal data. For example, the plurality of sets of fNIRS optodes 106 may be arranged as an array of source optodes 106A that extends from one longitudinal end side of the IED 200C to the other, and as an array of detector optodes 106B that extends from the one longitudinal end side of the IED 200C to the other. The source optodes 106A and the detector optodes 106B may alternate along the length direction of the IED 200C, and the optodes may be driven with time-multiplexing or spectral-multiplexing to generate fNIRS signal data for each of the plurality of sets of fNIRS optodes 106 that may have the same or different SDS. As explained previously, if the distance from the detector to the source is reduced, the penetration depth is lower. In some embodiments, brain activity may be captured at different depths in the temporal cortex when generating the filtered fNIRS signal data. Thus, for example, the optodes of the IED 200C may be driven as virtual optodes in different combinations corresponding to the plurality of sets of fNIRS optodes 106 *s* to generate the fNIRS signal data for the respective sets corresponding to different penetration depths.

As shown in FIGS. 2A-2B, the source optodes 106A (106A') may be disposed at one longitudinal end side of the IED 200A-B and the detector optodes 106B (106B') may be disposed at the other longitudinal end side of the IED 200A-B, such that the SDS between the source and the detector optodes of each set may be at least a predetermined distance (e.g., at least 1 centimeter). Further, as shown in FIGS. 2A-2C, the fNIRS optodes may be disposed on the IED 200A-C such that the fNIRS optodes are exposed to an external surface of the IED 200A-C and configured to be in contact with the inner surface of the ear canal 118 of the user when the IED 200A-C is worn by the user.

The configuration and operation of the plurality of sets of fNIRS optodes 106 (106') as shown in FIGS. 2A-2C is exemplary and not intended to be limiting. For example, the number of source optodes 106A (106A') that may be disposed on the IED 200A-C (or number of sets) is not intended to be limiting. Similarly, the number of detector optodes 106B (106B') that may be disposed on the IED 200A-C (or number of sets) is also not intended to be limiting. Thus, any number of the source optodes 106A, and the detector optodes 106B may be embedded in the IED 200A-C to define one or more the sets of fNIRS optodes 106 (including reciprocal sets) generating respective fNIRS signal data. Further, the size, shape, location, arrangement, and the like of the optodes is also not limited to what is exemplified in FIGS. 2A-2C.

The in-ear fNIRS device according to the present disclosure can be a continuous-wave system including one or more optodes (e.g., 690 and 830 nm optical wavelengths, 50 Hz sampling frequency) where the specific wavelengths fall into predetermined ranges (e.g., between ~650 nm-~780 nm, and between ~820 nm-~1000 nm) according to Beer-Lambert law principle. The IED 200 may measure baseline blood oxygenation along the length of the ear canal (e.g., ~1.5 cm) at two or more wavelengths via the Beer-Lambert law principle and estimate HbO and HbR saturation in the temporal lobe. Since the source and detector optodes 106 are embedded within the in-ear component, the curved optical path 107 captures brain activity from inside the ear-canal. Further, since the IED 200 may be provided for each ear, the fNIRS measurement technique may enable binaural measurement, and the information from the two cortical regions on the two sides can be simultaneously captured using the two IEDs 200 worn by the user. Still further, in some embodiments, as shown in FIGS. 2B-2C, multiple sets of detectors and sources may be embedded within the in-ear device to maximize the spatial distribution of the source-detector sets, and thereby enhance the penetration depth (via the virtual optode sets) and the signal-to noise ratios (via the reciprocal sets).

FIG. 3 is a block diagram of a cognitive load estimation system 300, in accordance with one or more embodiments. The cognitive load estimation system 300 may include the IED 301, and a cognitive load estimation device 350. The system 300 may optionally further include a sensor device 340. A network 370 may communicatively couple the IED 301, the cognitive load estimation device 350, the sensor device 340, or some combination thereof. The IEDs 200A-200C of FIGS. 2A-2C may be different embodiments of the IED 301 shown in FIG. 3.

The IED 301 fits within the ear canal 118 of the user near the eardrum 120 and captures various types of data from within the ear canal 118. Although FIG. 3 shows the system 300 including one IED 301, another embodiment of the system 300 may include two IEDs 301, one each for each ear of the user. As shown in FIG. 3, the IED 301 may include an audio transducer 302, one or more EEG electrodes 304, a set (e.g., pair) of fNIRS optodes including the source optode 106A and the detector optode 106B, an acoustic sensor 308, a motion sensor 310, a controller 312, a battery 314, a communication interface 316, and an acoustic sensor 324. These components of the IED 301 may be mounted to a circuit board (not shown) that connects the components to each other. In some embodiments, the IED 301 may be individualized to the anatomy of the user's ear canal 118 geometry. To create a customized solution, 3D geometries of the user's ear canal 118 may be obtained by using either traditional molding techniques, or 3D digital scanning techniques.

The audio transducer 302 is a speaker that generates sound from audio data and outputs the sound into the ear canal 118. The audio transducer 302 may be used to present audio signals to the user. Further, in some embodiments, the audio transducer 302 re-broadcasts sound from the local area detected by the acoustic sensor 324, such that the IED 301 provides hear-through functionality even though it is occluding the ear canal 118.

The one or more EEG electrodes 304 capture electrical charges that result from activity in brain cells of the brain of the user. The one or more EEG electrodes 304 may use the principle of differential amplification by recording voltage differences between different points that compares one active exploring electrode site with another neighboring or distant reference electrode. The electrical signals captured by the EEG electrodes 304 may be used to generate EEG signal data defining a waveform over time that represents the electrical activity that is taking place within the brain of the user. In some embodiments, the EEG electrodes 304 may be part of a group of electrodes that may be used to generate different types of electrograms of the brain, eye, heart, and the like (e.g., electroencephalography (EEG), electrocorticography (ECoG or iEEG), electrooculography (EOG), electroretinography (ERG), electrocardiogram (ECG)). As shown in FIG. 3, the EEG electrode 304 is positioned at a location on the IED 301 such that it contacts an inner surface of the user's ear canal 118 when the IED 301 is worn by the user.

In some embodiments, the EEG electrode 304 is a dry electrode that may be directly in contact with the anatomy of the user. A dry electrode does not need gel or some other type of medium or layer between the EEG electrode 304 and the tissue. The EEG electrode 304 may include hard material electrodes (e.g., including gold-plated brass, iridium oxide, etc.) or soft and/or stretchable material electrodes (e.g., including conductive textiles, conductive polymers, carbon allotropes such as graphene or carbon nanotubes, or poly(3, 4-ethylenedioxythiophene) polystyrene sulfonate (PEDOT: PSS). The number of the EEG electrodes 304 disposed on the IED 301 is not intended to be limiting. In some embodiments, the EEG electrode 304 may be excluded from IED 301, and instead be provided on another component of the cognitive load estimation system 300 that is external to the IED 301. In other embodiments, the IED 301 may include one, two, or more than two of the EEG electrodes 304.

The set of fNIRS optodes 106 are described above in connection with FIGS. 1 and 2, and detailed description thereof is omitted here. The embodiment in FIG. 3 shows one set of optodes including one source optode 106A and one detector optode 106B, that define the curved optical path 107. As may be evident from the above disclosure regarding the IEDs 200A-C in FIGS. 2A-2C, the number of optodes embedded on the IED 301, or the number of sets of the optodes in the IED 301 are not intended to be limiting. Also, as may be evident from the above disclosure regarding the IED 200A-C in FIGS. 2A-2C, the location, size, shape, and arrangement of the optodes on the IED 301 is not intended to be limiting so long as the IED 301 can be operated to generate the fNIRS signal data.

The controller 312 may perform processing to facilitate capturing of sensor data. For example, the controller 312 may control the one or more EEG electrodes 304 to receive the electrical signals captured by the EEG electrodes 304. In some embodiments, the controller 312 may include a differential amplifier to amplify a difference between voltage signals detected at the EEG electrodes 304. The controller 312 may also include an analog to digital converter (ADC) that converts the electrical signals from the EEG electrodes 304 into EEG signal data representing the brain activity of the user. As another example, the controller 312 may control the source optode 106A and the detector optode 106B of the set of optodes to receive electrical signals corresponding to the intensity of light detected by the detector optode 106B. The ADC of the controller 312 may then convert the electrical signals corresponding to the intensity of the light detected by the detector optode 106B into the (unfiltered) fNIRS signal data. The controller 312 may perform similar processing to generate fNIRS signal data (e.g., reciprocal data, additional data) corresponding to additional sets of fNIRS optodes 106 that may be embedded on the IED 301.

In some embodiments, the EEG and the fNIRS measurement techniques may be combined to subtract noise from true neural signal. EEG measures brain activity with high temporal resolution, but across a wide spatial range. By contrast, fNIRS measures the brain activity with low temporal resolution (constrained by the slow biological dynamics of blood flow changes) but in close spatial range. That is, data acquired from EEG electrodes is typically faster than fNIRS measurements. For example, a sampling rate for EEG measurements may be ~100°-2000 Hz, whereas a sampling rate for fNIRS measurements may be ~10-50 Hz. Thus, the EEG signal data may be captured at a faster rate (i.e., higher temporal resolution) than the fNIRS signal data. Further, the EEG signal data is generated by averaging the response corresponding to electrical firings for a group of neurons (e.g., millions of neurons), whereas the fNIRS signal data monitors the changes in oxygenation status of brain's cortex in local areas within the curved optical path 107 of the optodes. As a result, the fNIRS signal data is much more local (i.e., low spatial range) than the EEG signal data. By combining the signal data from the two different measurement techniques, a neural signal representing brain activity that provides both temporal and spatial specificity can be obtained. Further, by using such a bi-modal (i.e., fNIRS+EEG) approach, parts of the signal in the fNIRS signal data that are likely of a neural origin can be separated out (e.g., regressed, disentangled) from parts that are likely of a systemic origin (e.g., separate out hemodynamic changes in the blood oxygenation in the frontal cortex representing brain activity from hemodynamic changes in the blood oxygenation in the frontal cortex that represent systemic factors like increased blood pressure or increased heart rate due to consumption of caffeine). To implement this bi-modal approach, the controller 312 may be configured to time synchronize the operation of the fNIRS optodes 106 of the system 300 to capture the electrical signals representing the fNIRS signal data, with the operation of the EEG electrodes 304 of the system 300 to capture the electrical signals thereof representing the EEG signal data.

The controller 312 may also convert sensor data from other sensors (e.g., the acoustic sensor 308 and/or the motion sensor 310) into digital data representing waveforms. The controller 312 may be configured to perform additional processing to, e.g., play audio content, record audio content, capture sensor data, perform predetermined processing on the sensor data, and the like. The controller 312 may also include a digital to analog converter (DAC) that, e.g., converts digital audio data into analog audio data for rendering by the audio transducer 302. One or more of the features of the controller 312 may be performed by the controller 360 of the cognitive load estimation device 350.

The battery 314 provides power to the other components of the IED 301. The battery 314 allows the IED 301 to operate as a mobile device. The battery 314 may be rechargeable via wire or wirelessly.

The communication interface 316 facilitates (e.g., wireless) connection of the IED 301 to other devices, such as the cognitive load estimation device 350 via the network 370. For example, the communication interface 316 may transfer data (e.g., unfiltered fNIRS signal data, reciprocal fNIRS signal data, additional fNIRS signal data, filtered fNIRS signal data, EEG signal data) generated by the IED 301 to the cognitive load estimation device 350 for estimating a cognitive load of the user, and performing actions based on the estimation. The IED 301 may also receive data or other types of information from the cognitive load estimation device 350 via the communication interface 316. In some embodiments, the communication interface 316 includes an antenna and a transceiver.

In some embodiments, the system 300 may further include the sensor device 340 including one or more biometric sensors. The one or more biometric sensors of the sensor device 340 may include one or more of the fNIRS optodes 106, one or more of the EEG electrodes 304, or some combination thereof. The sensor device 140 may be a headcap or other wearable device that can be used to strap the one or more biometric sensors to be in contact with the skin of the user. The electrical signals captured by the one or more biometric sensors of the sensor device 340 may be used to generate, for example, the additional fNIRS signal data, the reciprocal fNIRS signal data the EEG signal data, or some combination thereof. In some embodiments, the sensor device 340 may correspond to a medical- or hospital-grade EEG monitoring system used for in-clinic EEG signal monitoring. In some embodiments, the sensor device 340 may correspond to a medical- or hospital-grade fNIRS monitoring system used for in-clinic fNIRS signal monitoring. The sensor device 340 may be used to supplement sensor data generated using the IED 301, and/or sensor data generated using the cognitive load estimation device 350, to generate the filtered fNIRS signal data and to estimate the cognitive load of the user.

The cognitive load estimation device 350 may estimate a cognitive load on the user. The cognitive load estimate device may include a controller 360. In some embodiments, the cognitive load estimation device 350 may also include one or more of the fNIRS optodes 106, one or more of the EEG electrodes 304, or some combination thereof. Some or all of the components and corresponding functionality of the cognitive load estimation device 350 may be subsumed by the IED 301. In some embodiments, the cognitive load estimation device 350 may receive data (e.g., EEG signal data, unfiltered fNIRS signal data, reciprocal fNIRS signal data, additional fNIRS signal data) from the IED 301 (and optionally, from the sensor device 340) via the network 370. The cognitive load estimation device 350 may further filter the fNIRS signal data (e.g., using the EEG signal data, and the reciprocal fNIRS signal data), estimate a cognitive load of the user based on the filtered data, and perform an action based on the estimated cognitive load of the user. That is, the cognitive load estimation device 350 may be configured to receive data recorded by the EEG electrodes 304, the sets of fNIRS optodes 106, and/or other sensors (e.g., from the IED 301, the sensor device 340) and generate the filtered fNIRS signal data for estimating and monitoring in real-time, the cognitive load of the user, and performing actions based on the estimation (e.g., instruct the controller 312 to adjust the SNR of an audio signal output to the speaker 302 of the IED 301 based on the estimated cognitive load).

Some embodiments of the IED 301 and the cognitive load estimation device 350 have different components than those described here. Similarly, in some cases, functions can be distributed among the components in a different manner than is described here. For example, one or more steps of the processing for generating the filtered fNIRS signal data based on the reciprocal fNIRS signal data, the additional fNIRS signal data, the EEG signal data, or some combination thereof, may be performed by the IED 301.

In one embodiment, the cognitive load estimation device 350 is a headset or head-mounted display (HMD), as discussed in greater detail below in connection with FIGS. 4A and 4B. Alternatively, the cognitive load estimation device 350 may be a device having computer functionality, such as a desktop computer, a laptop computer, a personal digital assistant (PDA), a mobile telephone, a smartphone, a tablet, an Internet of Things (IoT) device, a virtual conferencing device, a cuff, or another suitable device. In other embodiments, although not specifically shown in the figures, the cognitive load estimation device 350 is a headphone device (e.g., over the ear headphone), and a form factor of the cognitive load estimation device 350 may be designed to integrate a plurality of the fNIRS optodes 106 along a length of an earpiece of the headphone device.

The controller 360 may include various components that provide functionality for the cognitive load estimation. The components may include, e.g., one or more processors, a data store 362, a signal processing module 364, and a load estimation module 368. Some embodiments of the controller 360 have different components than those described here. Similarly, in some cases, functions can be distributed among the components in a different manner than is described here. In some embodiments, the functionality of the controller 360 may be subsumed, in whole or in part, by the controller 312 of the IED 301.

The data store 362 stores data (e.g., unfiltered fNIRS signal data, additional fNIRS signal data, reciprocal fNIRS signal data, filtered fNIRS signal data, EEG signal data, program instruction data corresponding to the various modules of the controller 360, and the like) used by the cognitive load estimation device 350. The data store 362 may also store data used by the IED 301. The data store 362 (e.g., a non-transitory computer-readable storage medium) and the one or more processors that operate in conjunction to carry out various functions attributed to the calibration device 350 as described herein. For example, the data store 362 may store one or more modules or applications embodied as instructions executable by the one or more processors of the controller 360. The instructions, when executed by the controller 360, cause the controller 360 to carry out the functions attributed to the various modules or applications of the controller 360.

The signal processing module 364 may be configured to process the fNIRS signal data and the EEG signal data. In some embodiments, the signal processing module 364 may be configured to receive the electrical signals recorded by the EEG electrodes 304 included in the IED(s) 301, in the sensor device 340, in the cognitive load estimation device 350, or some combination thereof. The signal processing module 364 may then generate the EEG signal data based on the received electrical signals recorded by the EEG electrodes 304 in the one or more devices. The signal processing module 364 may also be configured to directly receive the EEG signal data generated from the electrical signals recorded by the EEG electrodes 304 included in the IED(s) 301, in the sensor device 340, in the cognitive load estimation device 350, or some combination thereof (e.g., EEG signal data generated by the controller 312 of the IED 301). The signal processing module 364 may further store the received or generated EEG signal data in the data store 362.

Further, in some embodiments, the signal processing module 364 may be configured to receive the electrical signals recorded by the sets of fNIRS optodes 106 included in the IED(s) 301, in the sensor device 340, in the cognitive load estimation device 350, or some combination thereof. The signal processing module 364 may generate fNIRS signal data based on the received electrical signals recorded by the sets of fNIRS optodes 106. For example, for each set of fNIRS optodes 106, the signal processing module 364 may generate the corresponding fNIRS signal data (e.g., unfiltered fNIRS signal data, reciprocal fNIRS signal data, additional fNIRS signal data) based on the corresponding recorded electrical signals. The signal processing module 364 may also be configured to receive the fNIRS signal data generated from the electrical signals recorded by the sets of fNIRS optodes 106 included in the IED 301, in the sensor device 340, in the cognitive load estimation device 350, or some combination thereof (e.g., unfiltered fNIRS signal data, reciprocal fNIRS signal data, additional fNIRS signal data, generated by the controller 312 of the IED 301). The signal processing module 364 may further store the received or generated fNIRS signal data in the data store 362.

The signal processing module 364 may be further configured to process fNIRS signal data and EEG signal data to generate the filtered fNIRS signal data. To filter the (original, unfiltered) fNIRS signal data based on the reciprocal fNIRS signal data, the signal processing module 364 compares the bidirectional fNIRS signal data captured by the reciprocal sets of fNIRS optodes 106. By comparing the reciprocal fNIRS signals, the signal processing module 364 can ascertain the signal quality, and ascertain whether the signal is of a neural origin or if the signal is a part of a systemic response of the body. Based on the comparison, the signal processing module 364 subtracts noise from the original, unfiltered fNIRS signal data.

Further, to filter the (original, unfiltered) fNIRS signal data based on the EEG signal data, the signal processing module 364 analyzes the EEG signal data, where the fNIRS signal data is captured by the set of fNIRS optodes 106 in time synchronization (e.g., at the same time) with the capturing of the EEG signal data by the EEG electrodes 304. For example, the signal processing module 364 may analyze the phases of the EEG signal in predetermined frequency bands, and make estimates about the fNIRS signal data based on the analysis.

The signal processing module 364 (e.g., machine-learned model like a deep learning model, convolutional neural network, and the like) may thus ascertain (e.g., identify) parts of the signal in the fNIRS recording that are likely of a neural origin, from parts of the signal in the fNIRS recording that are likely of a systemic origin (e.g., ascertain hemodynamic changes in the blood oxygenation in the frontal cortex representing brain activity from hemodynamic changes in the blood oxygenation in the frontal cortex that represent systemic factors like increased blood pressure or increased heart rate due to consumption of caffeine). And based on the identification, the signal processing module 364 may regress out the signals corresponding to the systemic factors from the signals that are due to brain activity, thereby generating the filtered fNIRS signal data.

In some embodiments, the signal processing module 364 may be configured to utilize a multi-modal fusion mechanism for cognitive load estimation. For example, the cognitive load estimation device 350 may include pupillometry sensors (e.g., optical sensors, eye-tracking sensors) that may be disposed on a headset and positioned in front of the eye of the user to capture the pupil dilation departures from normal dilation parameters from the pupil. The signal processing module 364 may then use the pupil dilation information (that may be captured in time synchronization with the EEG signal data, and the fNIRS signal data) from the pupillometry sensor in combination with the EEG signal data and the fNIRS signal data to implement a multi-modal approach for cognitive load estimation.

The load estimation module 368 (e.g., machine-learned model like a deep learning model, convolutional neural network, and the like) is configured to estimate a cognitive load of the user. The load estimation module 368 is further configured to determine an action based on the estimation. In some embodiments, the load estimation module 368 estimates the cognitive load (e.g., listening effort, listener's intent, and the like) of the user based on the filtered fNIRS signal data (and/or EEG signal data). In some embodiments, a labeled dataset (i.e., training set) may be built based on concurrent measurements of EEG signal data and/or fNIRS signal data for a large number of subjects (e.g., more than 100 subjects) while the subjects go through incrementally higher (measured) levels of cognitive workload. In the training set, the measurement of the EEG signal data and the fNIRS signal data for the subjects may be time synchronized. A machine-learning engine may then train a model (e.g., a deep learning network) using the training set to obtain a feature matrix. The machine-learned model may thus be trained to classify a given input set of fNIRS signal data and EEG signal data (or one of the fNIRS signal data and EEG signal data) to estimate a corresponding level of cognitive load. Thus, for example, a pre-trained deep learning network model may use the EEG information and/or the fNIRS information to classify the level of cognitive load based on the captured EEG signals and/or fNIRS signals.

In some embodiments, the load estimation module 368 may continuously determine (based on real-time monitored, filtered fNIRS signal data) whether a current audio setting (e.g., beamforming setting, signal-to-noise ratio setting, and the like, of an audio signal output from the speaker 302 of the IED 301) has an estimated cognitive load that is higher than a threshold load. And in response to determining that the current audio setting has the estimated cognitive load higher than the threshold load, the load estimation module 368 may determine and apply a new adjusted audio setting, and then determine (based on real-time monitored, filtered fNIRS signal data) whether the new setting leads to a reduced cognitive load on the user that is lower than the threshold load.

More specifically, if the user is having difficulty in listening to someone in a crowded or noisy environment, the load estimation module 368, based on the filtered fNIRS signal data received from the signal processing module 364, may automatically determine (e.g., using a model) that user is having the difficulty. Further, the load estimation module 368 may determine and apply the new adjusted audio setting based on the determined level of difficulty the user is experiencing (i.e., the estimated cognitive load), and, e.g., automatically enhance the signal-to-noise ratio (or gain) of the audio playback for a specific direction that the listener is trying to listen to, and then determine again if the user's cognitive load has now reduced to an acceptable level with the new adjusted audio setting.

The load estimation module 368 may thus implement a gradual enhancement strategy (as opposed to binary), by being configured to continuously perform the adjustment to the audio setting, in real-time, based on the continuously monitored and estimated cognitive load of the user. The load estimation module 368 may thus determine how much enhancement is necessary, and what the right balance is for enhancing what the system 300 has determined as the target audio versus suppressing what the system 300 has determined as the non-target audio, so as to maximize the possibility that the user can experience reality as it really stands. The load estimation module 368 may thus enable an intelligent self-adjusted enhancement of a listening scenario, where the self-adjustment is based on the user's estimated cognitive load or listening effort. Some or all components of the load estimation device 350 may be located in the IED 301. That is, some or all the functionality of the load estimation device 350, may be performed by the IED 301. In other words, the controller 360 may be an embodiment of and subsumed by the controller 312.

The network 370 may include any combination of local area and/or wide area networks, using wired and/or wireless communication systems. In one embodiment, the network 370 uses standard communications technologies and/or protocols. For example, the network 370 includes communication links using technologies such as Ethernet, 802.11 (WiFi), worldwide interoperability for microwave access (WiMAX), 3G, 4G, 5G, code division multiple access (CDMA), digital subscriber line (DSL), BLUETOOTH, Near Field Communication (NFC), Universal Serial Bus (USB), or any combination of protocols. In some embodiments, all or some of the communication links of network 370 may be encrypted using any suitable technique or techniques.

Figure 4A:
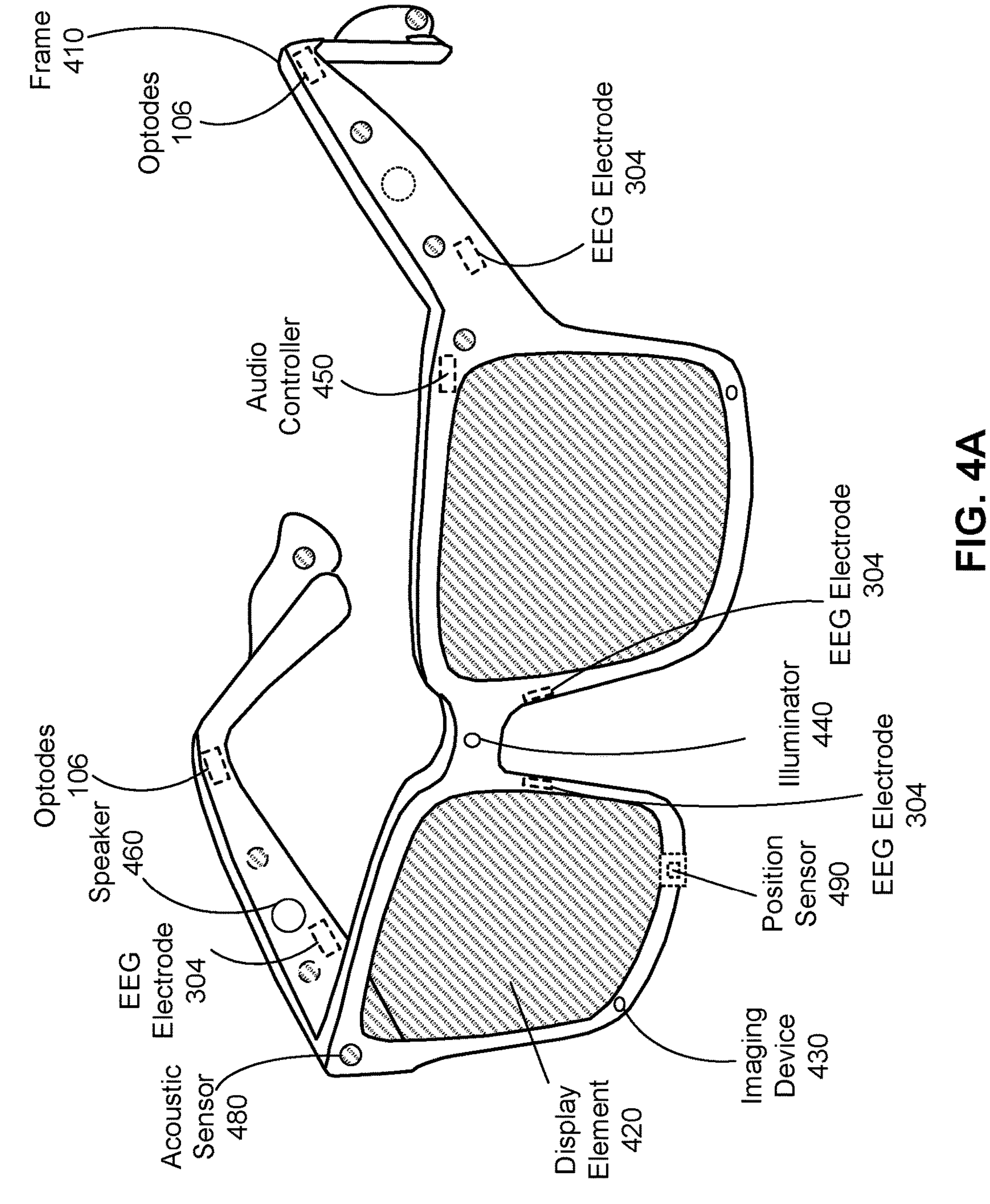
FIG. 4A is a perspective view of a headset implemented as an eyewear device, in accordance with one or more embodiments.

FIG. 4A is a perspective view of a headset 400 implemented as an eyewear device, in accordance with one or more embodiments. The headset 400 is an example of the cognitive load estimation device 350. In some embodiments, the eyewear device is a near eye display (NED). In general, the headset 400 may be worn on the face of a user such that content (e.g., media content) is presented using a display assembly and/or an audio system. However, the headset 400 may also be used such that media content is presented to a user in a different manner. Examples of media content presented by the headset 400 include one or more images, video, audio, or some combination thereof. The headset 400 includes a frame, and may include, among other components, a display assembly including one or more display elements 420, a depth camera assembly (DCA), an audio system, and a position sensor 490. While FIG. 4A illustrates the components of the headset 400 in example locations on the headset 400, the components may be located elsewhere on the headset 400, on a peripheral device paired with the headset 400 (e.g., on the IED 301, on the sensor device 340), or some combination thereof. Similarly, there may be more or fewer components on the headset 400 than what is shown in FIG. 4A.

A frame 410 holds the other components of the headset 400. The frame 410 includes a front part that holds the one or more display elements 420 and end pieces (e.g., temples) to attach to a head of the user. The front part of the frame 410 bridges the top of a nose of the user. The length of the end pieces may be adjustable (e.g., adjustable temple length) to fit different users. The end pieces may also include a portion that curls behind the ear of the user (e.g., temple tip, ear piece).

The frame 410 may include one or more biometric sensors. The biometric sensors may include one or more of the fNIRS optodes 106, one or more of the EEG electrodes 304, or some combination thereof. The embodiment shown in FIG. 4A illustrates two EEG electrodes 304 in the nosepads of the frame 410 and two EEG electrodes 304 on the temples. However, this is not intended to be limiting. Other embodiments of the headset 400 may have fewer or more EEG electrodes 304 that may be disposed at locations other than or in addition to that shown in FIG. 4A. Each EEG electrode 304 may be mounted so as to be in contact with the anatomy (e.g., nose bridge, temple) of the user when the headset 400 is worn by the user. In some embodiments, the headset 400 may be configured to generate the EEG signal data based on electrical signals captured by the EEG electrodes 304 in the IED 301, as well as based on the electrical signals that are captured by the EEG electrodes 304 in the headset 400. In some embodiments, the EEG electrodes 304 of the headset 400 may replace the EEG electrodes 304 of the IED 301 to capture the electrical signals for generating the EEG signal data.

The embodiment shown in FIG. 4A further illustrates two sets of fNIRS optodes 106 on the temple tips on both sides of the head of the user. Each optode set may be mounted so as to be in contact with the anatomy (e.g., skin behind the ear) of the user when the headset 400 is worn by the user. In some embodiments, the headset 400 may be configured to generate additional fNIRS signal data based on the two sets of fNIRS optodes 106 disposed on the headset 400 based, and cognitive load estimation device 350 may be configured to generate the filtered fNIRS signal data based on the (unfiltered) fNIRS signal data generated by the sets of fNIRS optodes 106 disposed on the IED 301, as well as based on the additional fNIRS signal data generated by the sets of fNIRS optodes 106 disposed on the headset 400. In some embodiments, the optodes of the headset 400 may replace or supplement the optodes of the IED 301 to capture the electrical signals for generating the fNIRS signal data. In some embodiments, a set of fNIRS optodes 106 may be distributed across multiple components of the cognitive load estimation system 300. For example, a source optode 106A of the set may be disposed on the frame 410 of the headset 400, while the corresponding detector optode 106B of the same set may be disposed on the IED 301 inside the ear canal 118 of the user. The fNIRS signal data generated by such a distributed set may be used in estimating the cognitive load of the user. Thus, in some embodiments, the cognitive load estimation system may include additional optodes 106 distributed along the length of the temple arms 410 of an AR/VR head-mounted display 400 or at the temple tips (e.g., at the pinna).

The one or more display elements 420 provide light to a user wearing the headset 400. As illustrated, the headset 400 includes the display element 420 for each eye of a user. In some embodiments, the display element 420 generates image light that is provided to an eyebox of the headset 400. The eyebox is a location in space that an eye of user occupies while wearing the headset 400. For example, the display element 420 may be a waveguide display. A waveguide display includes a light source (e.g., a two-dimensional source, one or more line sources, one or more point sources, etc.) and one or more waveguides. Light from the light source is in-coupled into the one or more waveguides which outputs the light in a manner such that there is pupil replication in an eyebox of the headset 400. In-coupling and/or outcoupling of light from the one or more waveguides may be done using one or more diffraction gratings. In some embodiments, the waveguide display includes a scanning element (e.g., waveguide, mirror, etc.) that scans light from the light source as it is in-coupled into the one or more waveguides. Note that in some embodiments, one or both of the display elements 420 are opaque and do not transmit light from a local area around the headset 400. The local area is the area surrounding the headset 400. For example, the local area may be a room that a user wearing the headset 400 is inside, or the user wearing the headset 400 may be outside and the local area is an outside area. In this context, the headset 400 generates VR content. Alternatively, in some embodiments, one or both of the display elements 420 are at least partially transparent, such that light from the local area may be combined with light from the one or more display elements to produce AR and/or MR content.

In some embodiments, the display element 420 does not generate image light, and instead is a lens that transmits light from the local area to the eyebox. For example, one or both of the display elements 420 may be a lens without correction (non-prescription) or a prescription lens (e.g., single vision, bifocal and trifocal, or progressive) to help correct for defects in a user's eyesight. In some embodiments, the display element 420 may be polarized and/or tinted to protect the user's eyes from the sun. In some embodiments, the display element 420 may include an additional optics block (not shown). The optics block may include one or more optical elements (e.g., lens, Fresnel lens, etc.) that direct light from display element 420 to the eyebox. The optics block may, e.g., correct for aberrations in some or all of the image content, magnify some or all of the image, or some combination thereof.

The DCA determines depth information for a portion of a local area surrounding the headset 400. The DCA includes one or more imaging devices 430 and a DCA controller (not shown in FIG. 4A), and may also include an illuminator 440. In some embodiments, the illuminator 440 illuminates a portion of the local area with light. The light may be, e.g., structured light (e.g., dot pattern, bars, etc.) in the infrared (IR), IR flash for time-of-flight, etc. In some embodiments, the one or more imaging devices 430 capture images of the portion of the local area that include the light from the illuminator 440. As illustrated, FIG. 4A shows a single illuminator 440 and two imaging devices 430. In alternate embodiments, there is no illuminator 440 and at least two imaging devices 430. The DCA controller computes depth information for the portion of the local area using the captured images and one or more depth determination techniques. The depth determination technique may be, e.g., direct time-of-flight (ToF) depth sensing, indirect ToF depth sensing, structured light, passive stereo analysis, active stereo analysis (uses texture added to the scene by light from the illuminator 440), some other technique to determine depth of a scene, or some combination thereof.

The DCA may include an eye tracking unit that determines eye tracking information. The eye tracking information may comprise information about a position and an orientation of one or both eyes (within their respective eye-boxes). The eye tracking unit may include one or more cameras. The eye tracking unit estimates an angular orientation of one or both eyes based on images captures of one or both eyes by the one or more cameras. In some embodiments, the eye tracking unit may also include one or more illuminators that illuminate one or both eyes with an illumination pattern (e.g., structured light, glints, etc.). The eye tracking unit may use the illumination pattern in the captured images to determine the eye tracking information. The headset 400 may prompt the user to opt in to allow operation of the eye tracking unit. For example, by opting in the headset 400 may detect, store, images of the user's eye or eye tracking information of the user.

In some embodiments, although not shown in FIG. 4A, the headset 400 may include one or more electrooculography (EOG) electrodes that are positioned close to the eyes of the user and that are configured to measure electrical signals representing the corneo-retinal standing potential that exists between the front and the back of one or both eyes of the user, to generate EOG signal data. The EOG signal data correlates in time with gaze direction of the user's eyes. The eye tracking unit may further be configured to determine the eye tracking information based on the generated EOG signal data using the EOG electrodes. In some embodiments, the eye tracking information, along with the EEG signal data from the electrodes 304, and the fNIRS signal data from the optodes 106, may together be used to, e.g., perform audio adjustments based on the user estimated cognitive load.

The audio system provides audio content. The audio system includes a transducer array, a sensor array, and an audio controller 450. However, in other embodiments, the audio system may include different and/or additional components. Similarly, in some cases, functionality described with reference to the components of the audio system can be distributed among the components in a different manner than is described here. For example, some or all of the functions of the controller may be performed by a remote server.

The sensor array detects sounds within the local area of the headset 400. The sensor array includes a plurality of acoustic sensors 480. An acoustic sensor 480 captures sounds emitted from one or more sound sources in the local area (e.g., a room). Each acoustic sensor is configured to detect sound and convert the detected sound into an electronic format (analog or digital). The acoustic sensors 480 may be acoustic wave sensors, microphones, sound transducers, or similar sensors that are suitable for detecting sounds.

In some embodiments, one or more acoustic sensors may be placed in an ear canal of each ear (e.g., in the IED 301, acting as binaural microphones). In some embodiments, the acoustic sensors 480 may be placed on an exterior surface of the headset 400, placed on an interior surface of the headset 400, separate from the headset 400 (e.g., part of some other device), or some combination thereof. The number and/or locations of the acoustic sensors 480 may be different from what is shown in FIG. 4A. For example, the number of acoustic detection locations may be increased to increase the amount of audio information collected and the sensitivity and/or accuracy of the information. The acoustic detection locations may be oriented such that the microphone is able to detect sounds in a wide range of directions surrounding the user wearing the headset 400.

The audio controller 450 processes information from the sensor array that describes sounds detected by the sensor array. The audio controller 450 may comprise a processor and a computer-readable storage medium. The audio controller 450 may be configured to generate direction of arrival (DOA) estimates, generate acoustic transfer functions (e.g., array transfer functions and/or head-related transfer functions), track the location of sound sources, form beams in the direction of sound sources, classify sound sources, generate sound filters for the speakers 460, or some combination thereof. In some embodiments, the audio controller 450 may subsume some or all of the functionality provided by the controller 360 of the cognitive load estimation device 350, and/or by the controller 312 of the IED 301. The audio controller 450 may thus be configured to perform the real-time cognitive load estimation. In some embodiments, some or all of the functionality of the audio controller 450 may be provided by the controller 312 of the IED 301.

The position sensor 490 generates one or more measurement signals in response to motion of the headset 400. The position sensor 490 may be located on a portion of the frame 410 of the headset 400. The position sensor 490 may include an inertial measurement unit (IMU). Examples of the position sensor 490 include: one or more accelerometers, one or more gyroscopes, one or more magnetometers, another suitable type of sensor that detects motion, a type of sensor used for error correction of the IMU, or some combination thereof. The position sensor 490 may be located external to the IMU, internal to the IMU, or some combination thereof.

In some embodiments, the headset 400 may provide for simultaneous localization and mapping (SLAM) for a position of the headset 400 and updating of a model of the local area. For example, the headset 400 may include a passive camera assembly (PCA) that generates color image data. The PCA may include one or more RGB cameras that capture images of some or all of the local area. In some embodiments, some or all of the imaging devices 430 of the DCA may also function as the PCA. The images captured by the PCA and the depth information determined by the DCA may be used to determine parameters of the local area, generate a model of the local area, update a model of the local area, or some combination thereof. Furthermore, the position sensor 490 tracks the position (e.g., location and pose) of the headset 400 within the room.

Figure 4B:
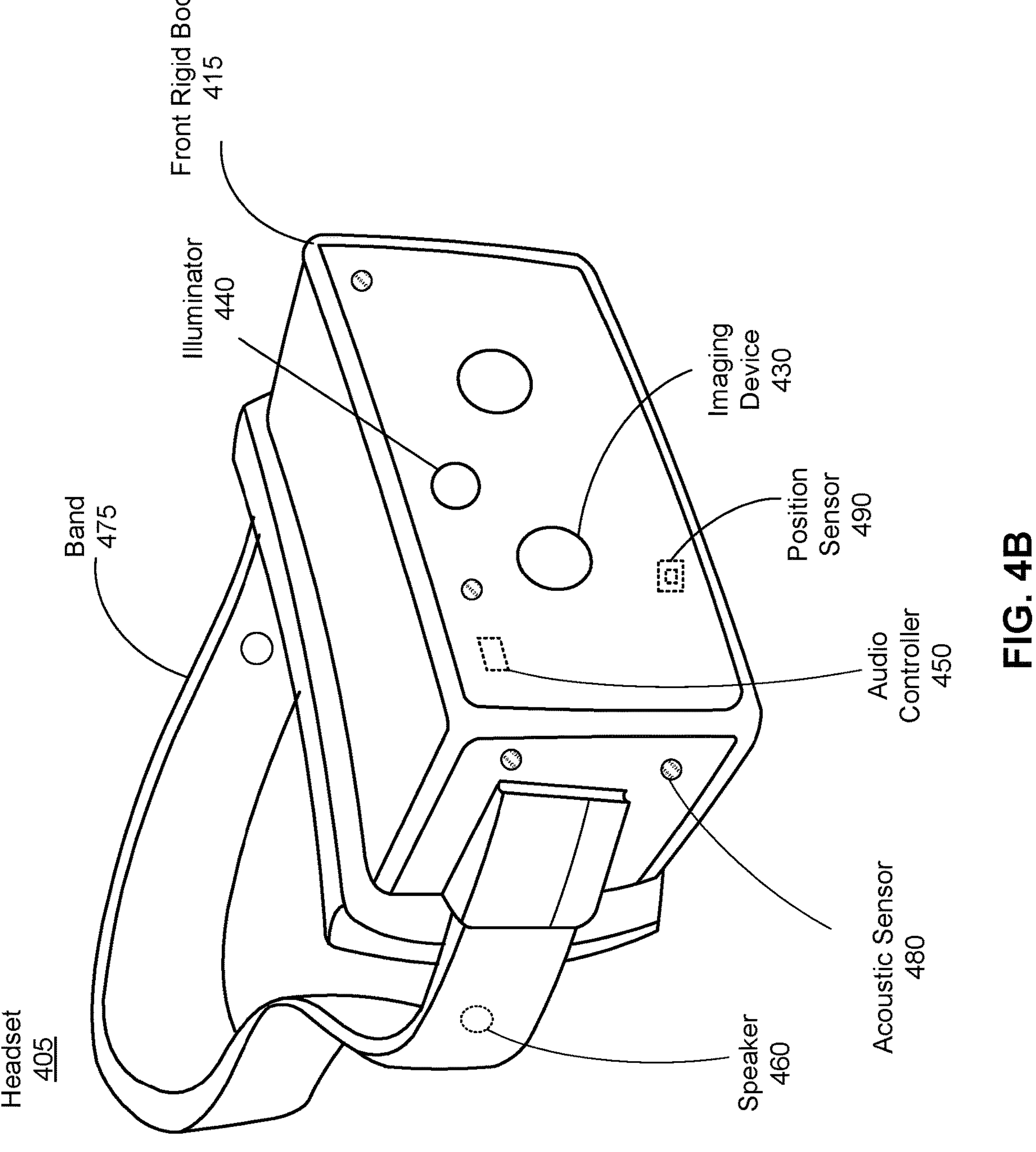
FIG. 4B is a perspective view of a headset implemented as a HMD, in accordance with one or more embodiments.

FIG. 4B is a perspective view of a headset 405 implemented as a HMD, in accordance with one or more embodiments. In embodiments that describe an AR system and/or a MR system, portions of a front side of the HMD are at least partially transparent in the visible band (~380 nm to 750 nm), and portions of the HMD that are between the front side of the HMD and an eye of the user are at least partially transparent (e.g., a partially transparent electronic display).

The HMD includes a front rigid body 415 and a band 475. The headset 405 includes many of the same components described above with reference to FIG. 4A, but modified to integrate with the HMD form factor. For example, the HMD includes a display assembly, a DCA, an audio system, EEG electrodes, EOG electrodes, and the position sensor 490. FIG. 4B shows the illuminator 440, a plurality of the speakers 460, a plurality of the imaging devices 430, a plurality of the acoustic sensors 480, and the position sensor 490. The speakers 460 may be located in various locations, such as coupled to the band 475 (as shown), coupled to the front rigid body 415, or may be configured to be inserted within the ear canal of a user.

Figure 5:
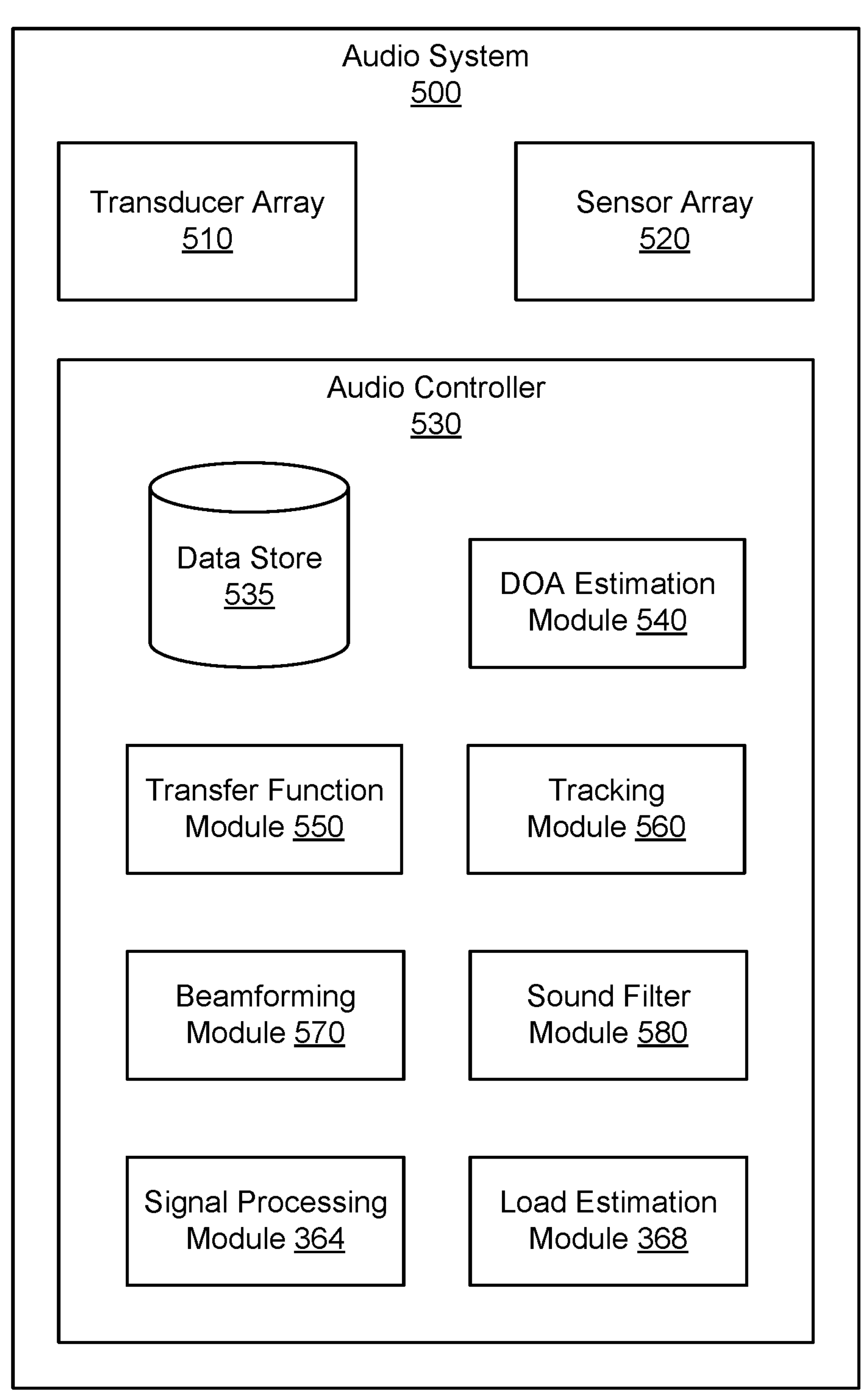
FIG. 5 is a block diagram of an audio system, in accordance with one or more embodiments.

FIG. 5 is a block diagram of an audio system 500, in accordance with one or more embodiments. The audio system 500 may subsume the functionality, in whole or in part, of the controller 360 of the cognitive load estimation device 350, and/or the functionality, in whole or in part, of the controller 312 of the IED 301. The audio system 500 generates one or more acoustic transfer functions for a user. The audio system 500 may then use the one or more acoustic transfer functions to generate audio content for the user. In the embodiment of FIG. 5, the audio system 500 includes a transducer array 510, a sensor array 520, and an audio controller 530. Some embodiments of the audio system 500 have different components than those described here. Similarly, in some cases, functions can be distributed among the components in a different manner than is described here.

The transducer array 510 is configured to present audio content. The transducer array 510 includes a plurality of transducers. A transducer is a device that provides audio content. A transducer may be, e.g., a speaker (e.g., the speaker 302, the speaker 460), a tissue transducer, some other device that provides audio content, or some combination thereof. A tissue transducer may be configured to function as a bone conduction transducer or a cartilage conduction transducer. The transducer array 510 may present audio content via air conduction (e.g., via one or more speakers), via bone conduction (via one or more bone conduction transducer), via cartilage conduction audio system (via one or more cartilage conduction transducers), or some combination thereof. In some embodiments, the transducer array 510 may include one or more transducers to cover different parts of a frequency range. For example, a piezoelectric transducer may be used to cover a first part of a frequency range and a moving coil transducer may be used to cover a second part of a frequency range.

The bone conduction transducers generate acoustic pressure waves by vibrating bone/tissue in the user's head. A bone conduction transducer may be coupled to a portion of a headset, and may be configured to be behind the auricle coupled to a portion of the user's skull. The bone conduction transducer receives vibration instructions from the audio controller 530, and vibrates a portion of the user's skull based on the received instructions. The vibrations from the bone conduction transducer generate a tissue-borne acoustic pressure wave that propagates toward the user's cochlea, bypassing the eardrum.

The cartilage conduction transducers generate acoustic pressure waves by vibrating one or more portions of the auricular cartilage of the ears of the user. A cartilage conduction transducer may be coupled to a portion of a headset, and may be configured to be coupled to one or more portions of the auricular cartilage of the ear. For example, the cartilage conduction transducer may couple to the back of an auricle of the ear of the user. The cartilage conduction transducer may be located anywhere along the auricular cartilage around the outer ear (e.g., the pinna, the tragus, some other portion of the auricular cartilage, or some combination thereof). Vibrating the one or more portions of auricular cartilage may generate: airborne acoustic pressure waves outside the ear canal; tissue born acoustic pressure waves that cause some portions of the ear canal to vibrate thereby generating an airborne acoustic pressure wave within the ear canal; or some combination thereof. The generated airborne acoustic pressure waves propagate down the ear canal toward the ear drum.

The transducer array 510 generates audio content in accordance with instructions from the audio controller 530. In some embodiments, the audio content is spatialized. Spatialized audio content is audio content that appears to originate from a particular direction and/or target region (e.g., an object in the local area and/or a virtual object). For example, spatialized audio content can make it appear that sound is originating from a virtual singer across a room from a user of the audio system 500. The transducer array 510 may be coupled to a wearable device (e.g., the IED 301, the cognitive load estimation device 350, the headset 400, or the headset 405). In alternate embodiments, transducer array 510 may be a plurality of speakers that are separate from the wearable device (e.g., coupled to an external console).

The sensor array 520 detects sounds within a local area surrounding the sensor array 520. The sensor array 520 may include a plurality of acoustic sensors (e.g., the sensors 308, 324, and/or 480) that each detect air pressure variations of a sound wave and convert the detected sounds into an electronic format (analog or digital). The plurality of acoustic sensors may be positioned on a headset (e.g., cognitive load estimation device 350 implemented as headphones, the headset 400, and/or the headset 405), on a user (e.g., the IED 301 in an ear canal of the user), on a neckband, or some combination thereof. An acoustic sensor may be, e.g., a microphone, a vibration sensor, an accelerometer, or any combination thereof. In some embodiments, the sensor array 520 is configured to monitor the audio content generated by the transducer array 510 using at least some of the plurality of acoustic sensors. Increasing the number of sensors may improve the accuracy of information (e.g., directionality) describing a sound field produced by the transducer array 510 and/or sound from the local area.

The audio controller 530 controls operation of the audio system 500. In the embodiment of FIG. 5, the audio controller 530 includes a data store 535, a DOA estimation module 540, a transfer function module 550, a tracking module 560, a beamforming module 570, a sound filter module 580. In an embodiment where the controller 530 subsumes functionality of the load estimation device 350, the audio controller 550 may further include the signal processing module 364, and the load estimation module 368, and the data store 535 may store data store in the data store 362. Detailed description of components and features of the audio controller 530 that are already discussed above in connection with FIG. 3 are omitted here to avoid repetition. The audio controller 530 may be located inside a headset, a headphone, and/or the IED 301 in some embodiments. Some embodiments of the audio controller 530 have different components than those described here. Similarly, functions can be distributed among the components in different manners than described here. For example, some functions of the controller 530 may be performed external to the headset. The user may opt in to allow the audio controller 530 to transmit data captured by the headset to systems external to the headset, and the user may select privacy settings controlling access to any such data.

The data store 535 stores data for use by the audio system 500. Data in the data store 535 may include sounds recorded in the local area of the audio system 500, audio content, head-related transfer functions (HRTFs), transfer functions for one or more sensors, array transfer functions (ATFs) for one or more of the acoustic sensors, sound source locations, virtual model of local area, direction of arrival estimates, sound filters, and other data relevant for use by the audio system 500, or any combination thereof. Data in the data store 535 may also include data that is stored in the data store 362 and that is related to the cognitive load estimation operation.

The DOA estimation module 540 is configured to localize sound sources in the local area based in part on information from the sensor array 520. Localization is a process of determining where sound sources are located relative to the user of the audio system 500. The DOA estimation module 540 performs a DOA analysis to localize one or more sound sources within the local area. The DOA analysis may include analyzing the intensity, spectra, and/or arrival time of each sound at the sensor array 520 to determine the direction from which the sounds originated. In some cases, the DOA analysis may include any suitable algorithm for analyzing a surrounding acoustic environment in which the audio system 500 is located.

For example, the DOA analysis may be designed to receive input signals from the sensor array 520 (or from the optodes or electrodes in the IED 301, the sensor device 340, the cognitive load estimation device 350, the headset 400, the headset 405, or some combination thereof) and apply digital signal processing algorithms to the input signals to estimate a direction of arrival. These algorithms may include, for example, delay and sum algorithms where the input signal is sampled, and the resulting weighted and delayed versions of the sampled signal are averaged together to determine a DOA. A least mean squared (LMS) algorithm may also be implemented to create an adaptive filter. This adaptive filter may then be used to identify differences in signal intensity, for example, or differences in time of arrival. These differences may then be used to estimate the DOA. In another embodiment, the DOA may be determined by converting the input signals into the frequency domain and selecting specific bins within the time-frequency (TF) domain to process. Each selected TF bin may be processed to determine whether that bin includes a portion of the audio spectrum with a direct path audio signal. Those bins having a portion of the direct-path signal may then be analyzed to identify the angle at which the sensor array 520 received the direct-path audio signal. The determined angle may then be used to identify the DOA for the received input signal. Other algorithms not listed above may also be used alone or in combination with the above algorithms to determine DOA.

In some embodiments, the DOA estimation module 540 may also determine the DOA with respect to an absolute position of the audio system 500 (or of the IED 301, or the headset 400 or 405) within the local area. The position of the sensor array 520 may be received from an external system (e.g., some other component of a headset, an artificial reality console, a mapping server, a position sensor (e.g., the position sensor 490), etc.). The external system may create a virtual model of the local area, in which the local area and the position of the audio system 500 are mapped. The received position information may include a location and/or an orientation of some or all of the audio system 500 (e.g., of the sensor array 520). The DOA estimation module 540 may update the estimated DOA based on the received position information.

The Transfer function module 550 is configured to generate one or more acoustic transfer functions. Generally, a transfer function is a mathematical function giving a corresponding output value for each possible input value. Based on parameters of the detected sounds, the transfer function module 550 generates one or more acoustic transfer functions associated with the audio system. The acoustic transfer functions may be array transfer functions (ATFs), head-related transfer functions (HRTFs), other types of acoustic transfer functions, or some combination thereof. An ATF characterizes how the microphone receives a sound from a point in space.

An ATF includes a number of transfer functions that characterize a relationship between the sound source and the corresponding sound received by the acoustic sensors in the sensor array 520. Accordingly, for a sound source there is a corresponding transfer function for each of the acoustic sensors in the sensor array 520. And collectively the set of transfer functions is referred to as an ATF. Accordingly, for each sound source there is a corresponding ATF. Note that the sound source may be, e.g., someone or something generating sound in the local area, the user, or one or more transducers of the transducer array 510. The ATF for a particular sound source location relative to the sensor array 520 may differ from user to user due to a person's anatomy (e.g., ear shape, shoulders, etc.) that affects the sound as it travels to the person's ears. Accordingly, the ATFs of the sensor array 520 are personalized for each user of the audio system 500.

In some embodiments, the transfer function module 550 determines one or more HRTFs for a user of the audio system 500. The HRTF characterizes how an ear receives a sound from a point in space. The HRTF for a particular source location relative to a person is unique to each ear of the person (and is unique to the person) due to the person's anatomy (e.g., ear shape, shoulders, etc.) that affects the sound as it travels to the person's ears. In some embodiments, the transfer function module 550 may determine HRTFs for the user using a calibration process. In some embodiments, the transfer function module 550 may provide information about the user to a remote system. The user may adjust privacy settings to allow or prevent the transfer function module 550 from providing the information about the user to any remote systems. The remote system determines a set of HRTFs that are customized to the user using, e.g., machine learning, and provides the customized set of HRTFs to the audio system 500.

The tracking module 560 is configured to track locations of one or more sound sources. The tracking module 560 may compare current DOA estimates and compare them with a stored history of previous DOA estimates. In some embodiments, the audio system 500 may recalculate DOA estimates on a periodic schedule, such as once per second, or once per millisecond. The tracking module may compare the current DOA estimates with previous DOA estimates, and in response to a change in a DOA estimate for a sound source, the tracking module 560 may determine that the sound source moved. In some embodiments, the tracking module 560 may detect a change in location based on visual information received from the headset or some other external source. The tracking module 560 may track the movement of one or more sound sources over time. The tracking module 560 may store values for a number of sound sources and a location of each sound source at each point in time. In response to a change in a value of the number or locations of the sound sources, the tracking module 560 may determine that a sound source moved. The tracking module 560 may calculate an estimate of the localization variance. The localization variance may be used as a confidence level for each determination of a change in movement.

The beamforming module 570 is configured to process one or more ATFs to selectively emphasize sounds from sound sources within a certain area while de-emphasizing sounds from other areas. In analyzing sounds detected by the sensor array 520, the beamforming module 570 may combine information from different acoustic sensors to emphasize sound associated from a particular region of the local area while deemphasizing sound that is from outside of the region. The beamforming module 370 may isolate an audio signal associated with sound from a particular sound source from other sound sources in the local area based on, e.g., the information from the load estimation module 368 for reducing the user's cognitive load, different DOA estimates from the DOA estimation module 540 and the tracking module 560, eye tracking information from the eye tracking unit, the (filtered) fNIRS signal data, the EEG signal data, EOG signal data, or some combination thereof. In some embodiments, the beamforming module 570 may isolate an audio signal associated with sound from a particular sound source based on a multi-modal fusion approach including the eye tracking information (pupillometry information) generated by the eye tracking unit of the headset 400/405 or device 350, based on the EEG signal data corresponding to the EEG electrodes 304, based on the fNIRS signal data corresponding to the sets of fNIRS optodes 106, based on the filtered fNIRS signal data generated by the signal processing module 364, based on the analysis performed by the load estimation module 368, or some combination thereof. The beamforming module 570 may thus selectively analyze discrete sound sources in the local area. In some embodiments, the beamforming module 570 may enhance a signal from a sound source. For example, the beamforming module 570 may apply sound filters which eliminate signals above, below, or between certain frequencies. Signal enhancement acts to enhance sounds associated with a given identified sound source relative to other sounds detected by the sensor array 520.

The sound filter module 580 determines sound filters for the transducer array 510. In some embodiments, the sound filters cause the audio content to be spatialized, such that the audio content appears to originate from a target region. The sound filter module 580 may use HRTFs and/or acoustic parameters to generate the sound filters. The acoustic parameters describe acoustic properties of the local area. The acoustic parameters may include, e.g., a reverberation time, a reverberation level, a room impulse response, etc. In some embodiments, the sound filter module 580 calculates one or more of the acoustic parameters. In some embodiments, the sound filter module 580 requests the acoustic parameters from a mapping server. The sound filter module 580 provides the sound filters to the transducer array 510 (or to the speakers of the IED 301, the device 350, the headset 400, the headset 405, or some combination thereof). In some embodiments, the sound filters may cause positive or negative amplification of sounds as a function of frequency.

Figure 6:
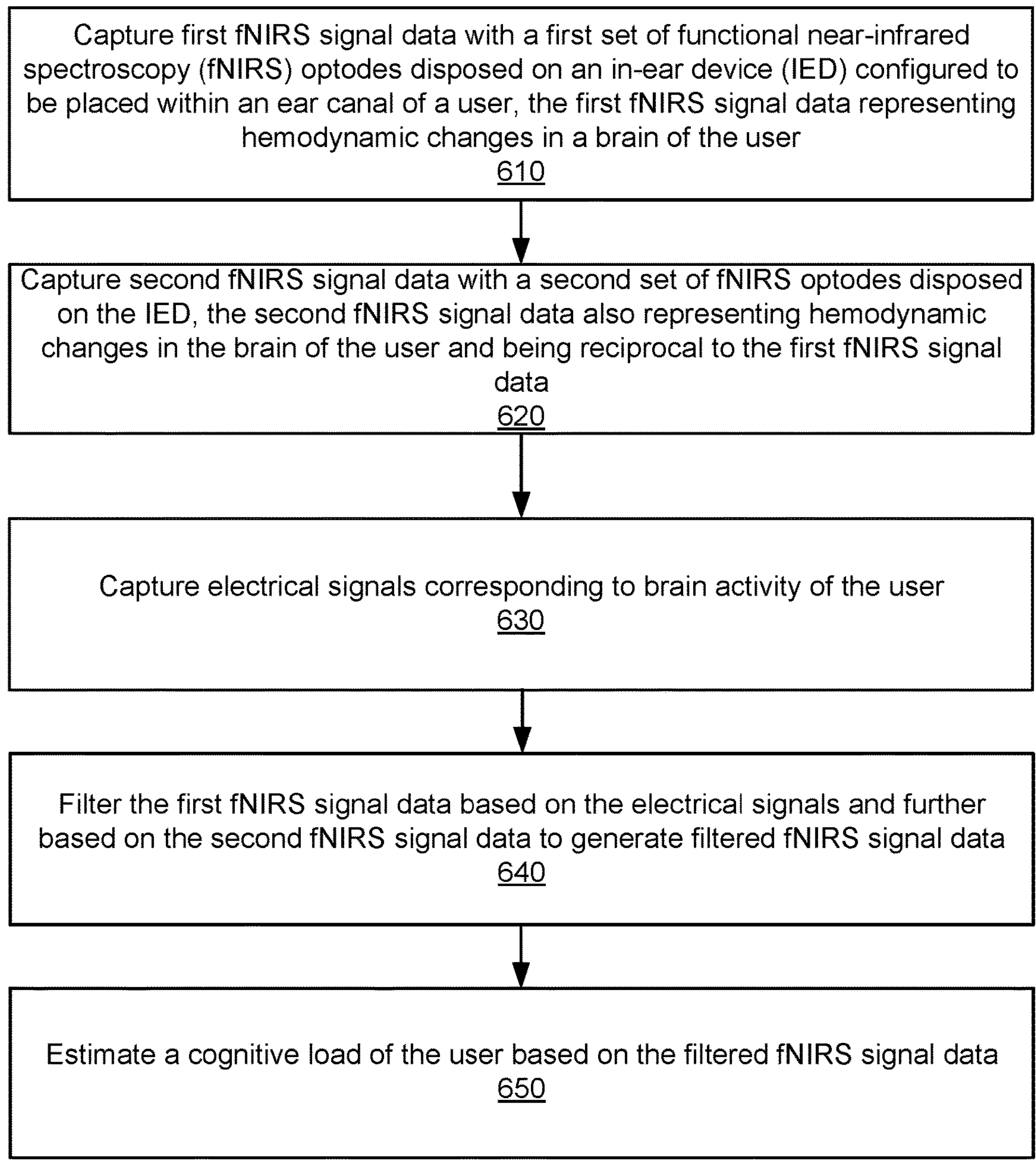
FIG. 6 is a flowchart of a method for estimating a cognitive load of the user, in accordance with one or more embodiments.

FIG. 6 is a flowchart of method 600 for estimating a cognitive load of the user, in accordance with one or more embodiments. The process shown in FIG. 6 may be performed by components of the cognitive load estimation system 300 (e.g., controller 315, controller 360). Other entities (e.g., the audio controller 450, the audio controller 530) may perform some or all of the steps in FIG. 6 in other embodiments. Embodiments may include different and/or additional steps, or perform the steps in different orders.

The cognitive load estimation system 300 captures 610 first fNIRS signal data with a first set of fNIRS optodes 106. The first set of fNIRS optodes 106 may be disposed on the IED 301 configured to be placed within the ear canal 118 of a user. The first fNIRS signal data may represent hemodynamic changes in a brain of the user. For example, using a first set of fNIRS optodes 106 including a source optode 106A and a detector optode 106B, the controller 312 may capture the first fNIRS signal data corresponding to a first curved optical path. Operation of the optodes 106A and the detector optode 106B of the first set may be time-multiplexed or spectrally multiplexed, and time-synchronized to generate the (original, unfiltered) first fNIRS signal data. That is, the changes in oxy-hemoglobin and deoxy-hemoglobin may be measured non-invasively from inside the ear-canal using (one or more) source-detector pairs or sets of optodes via time multiplexing or spectral-multiplexing.

The cognitive load estimation system 300 captures 620 second fNIRS signal data with a second set of fNIRS optodes 106' . . . . The second set of fNIRS optodes 106' may also be disposed on the IED 301, and the second fNIRS signal data may also represent hemodynamic changes in the brain of the user. For example, using a second set of optodes 106' including a source optode 106A' and a detector optode 106B', the controller 312 may capture the second (reciprocal) fNIRS signal data corresponding to a second curved optical path that is reciprocal to the first optical path. That is, the first and second sets of optodes may be reciprocal sets, and the captured fNIRS signal data of the two sets is reciprocal (e.g., bidirectional) as opposed to unidirectional, where the bidirectional fNIRS signal data captured by the reciprocal sets can be compared to correct for measurement errors, and separate true neural signal from noise caused by systemic factors. Operation of the source optode 106A' and the detector optode 1063 of the reciprocal set may also be time-multiplexed or spectrally multiplexed, and time-synchronized to generate the reciprocal (second) fNIRS signal data. The reciprocal (second) fNIRS signal data may be captured time interleaved with the first fNIRS signal data captured by the first set of the fNIRS optodes 106.

The cognitive load estimation system 300 captures 630 electrical signals corresponding to the brain activity of the user. At block 630, the controller 312 or 360 may capture the EEG signal data generated by the EEG electrodes 304 in time synchronization (e.g., at the same time) with the capturing of the first fNIRS signal data by the first set of fNIRS optodes 106 at block 610. By utilizing the temporal resolution coming from the EEG signals in conjunction with the blood flow oxygenations from the fNIRS signals that characterize hemodynamics from a device placed inside the ear-canal, the cognitive load is predicted more accurately by separating out the changes in blood oxygenation or deoxygenation caused by systemic factors as opposed to the changes having a true neural origin.

The cognitive load estimation system 300 filters 640 the first fNIRS signal data captured at block 610 based on the electrical signals captured at block 630 and further based on the second fNIRS signal data captured at block 620. For example, the signal processing module 364 may compare the bidirectional (i.e., first and second) fNIRS signal data captured by the reciprocal sets of fNIRS optodes 106 and 106' to ascertain the signal quality and ascertain whether the signal is of a neural origin or if part of the signal is due to a systemic response of the body. Based on the comparison, the signal processing module 364 corrects any error in the measurement of the original, unfiltered (first) fNIRS signal data by subtracting out the noise signal.

Further, the signal processing module 364 may compare the first fNIRS signal data captured at 610 with the EEG signal data captured at 630. Based on the comparison, the signal processing module 364 may ascertain (e.g., identify) parts of the signal in the first fNIRS signal data captured at 610 that are likely of a neural origin, from parts of the signal that are likely of a systemic origin. And based on the identification, the signal processing module 364 may regress out the signals corresponding to the systemic factors from the signals that are due to brain activity, thereby generating the filtered fNIRS signal data 640.

The cognitive load estimation system 300 estimates 650 the cognitive load (e.g., listening effort, listener's intent, and the like) of the user based on the filtered fNIRS signal data generated at 640. For example, the signal processing module 364 may apply a model to the filtered fNIRS signal data, where the model is trained to output an estimated measure of the cognitive load of the user based on the input filtered fNIRS signal data. And based on the estimated cognitive load, the cognitive load estimate system 300 may perform an action. For example, the cognitive load estimation system may adjust a SNR of an audio signal output to a speaker (e.g., speaker 302 of the IED 301).

The in-ear-canal-placement approach realizes a wearable in-ear fNIRS technique to estimate blood oxygenation and deoxygenation in the left or right temporal lobe (e.g., targeting recording from left or right STG), and predict the cognitive load (e.g., listening effort, listening fatigue) the user is experiencing based on the estimated changes in blood oxygenation or deoxygenation. Further, since the technique utilizes an in-ear device, contrary to conventional techniques, the fNIRS signal measurement technique according to the present disclosure remains suitable for individuals across a range of skin pigmentations and hair coarseness levels.

Additional Configuration Information

The foregoing description of the embodiments has been presented for illustration; it is not intended to be exhaustive or to limit the patent rights to the precise forms disclosed. Persons skilled in the relevant art can appreciate that many modifications and variations are possible considering the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A system, comprising:

an in-ear device (IED) configured to be placed within an ear canal of a user, the IED including a first set of functional near-infrared spectroscopy (fNIRS) optodes that are configured to capture first fNIRS signal data representing hemodynamic changes in a brain of the user;

at least one electroencephalography (EEG) electrode configured to capture electrical signals corresponding to brain activity of the user;

a controller configured to:

filter the first fNIRS signal data based in part on the electrical signals to generate filtered fNIRS signal data;

use a machine-learned model to estimate an amount of blood oxygenation change in a superior temporal gyrus of the user based on the filtered fNIRS signal data;

determine that the estimate of the amount of blood oxygenation change satisfies a threshold condition; and adjust an audio setting of an audio signal of the IED based on the satisfaction of the threshold condition; and a speaker configured to present the adjusted audio signal of the IED to the user.

2. The system of claim 1, wherein the audio setting corresponds to a signal-to-noise ratio of the audio signal.

3. The system of claim 1, wherein the first set of fNIRS optodes includes:

a first source optode configured to transmit light into a head of the user along a first optical path; and a first detector optode configured to detect the light transmitted by the first source optode.

4. The system of claim 3, wherein the IED further includes a second set of fNIRS optodes configured to capture second fNIRS signal data representing hemodynamic changes in the brain of the user, the second set of fNIRS optodes including:

a second source optode configured to transmit the light into the head of the user along a second optical path; and a second detector optode configured to detect the light transmitted by the second source optode, wherein the second optical path is reciprocal to the first optical path.

5. The system of claim 4, wherein a wavelength of the light transmitted by the second source optode is the same as a wavelength of the light transmitted by the first source optode.

6. The system of claim 4, wherein the first source optode and the second detector optode are disposed adjacent to each other at a first end side of the IED, and wherein the first detector optode and the second source optode are disposed adjacent to each other at a second end side of the IED, and wherein a distance between the first detector optode and the first detector optode, and a distance between the second source optode and the second detector optode are more than a predetermined distance.

7. The system of claim 4, wherein the controller is configured to generate the filtered fNIRS signal data by filtering the first fNIRS signal data based on the electrical signals and further based on the second fNIRS signal data.

8. The system of claim 7, further comprising a headset that is configured to be worn by the user, and that includes a third set of fNIRS optodes configured to capture third fNIRS signal data, wherein the controller is configured to generate the filtered fNIRS signal data by filtering the first fNIRS signal data based on the electrical signals, the second fNIRS signal data, and further based on the third fNIRS signal data.

9. The system of claim 1, wherein the first set of fNIRS optodes includes:

a plurality of first source optodes configured to respectively transmit light at different wavelengths into a head of the user; and at least one first detector optode configured to detect the light transmitted by the plurality of first source optodes at the different wavelengths, wherein the controller is configured to generate the first fNIRS signal data based on fNIRS signals captured using the plurality of first source optodes.

10. The system of claim 9, wherein the plurality of first source optodes are disposed at one longitudinal end side of the IED, and the at least one first detector optode is disposed at the other longitudinal end side of the IED.

11. The system of claim 1, wherein the at least one EEG electrode is disposed on the IED so as to be in contact with an inner surface of the ear canal when the IED is worn by the user.

12. The system of claim 1, further comprising a headset configured to be worn by the user, wherein the at least one EEG electrode includes a first electrode and a second electrode, the first electrode being disposed on the headset so as to be in contact with a head of the user when the headset is worn by the user.

13. The system of claim 12, wherein the second electrode is disposed on the IED, and wherein the controller configured to generate the filtered fNIRS signal data by filtering the first fNIRS signal data based on electrical signals generated by both the first electrode and the second electrode.

14. An in-ear device (IED) configured to be placed within an ear canal of a user, the IED comprising:

a first set of functional near-infrared spectroscopy (fNIRS) optodes that are configured to capture first fNIRS signal data representing hemodynamic changes in a brain of the user;

at least one electroencephalography (EEG) electrode that is disposed on the IED so as to be in contact with an inner surface of the ear canal, and that is configured to capture electrical signals corresponding to brain activity of the user;

a controller configured to:

filter the first fNIRS signal data based in part on the electrical signals to generate filtered fNIRS signal data;

use a machine-learned model to estimate an amount of blood oxygenation change in a superior temporal gyrus of the user based on the filtered fNIRS signal data;

determine that the estimate of the amount of blood oxygenation change satisfies a threshold condition; and adjust an audio setting of an audio signal of the IED based on the satisfaction of the threshold condition; and a speaker configured to present the adjusted audio signal of the IED to the user.

15. The IED of claim 14, wherein the first set of fNIRS optodes includes:

at least one first source optode configured to transmit light at a plurality of wavelengths into a head of the user along a first optical path; and a first detector optode configured to detect the light transmitted by the at least one first source optode at the plurality of wavelengths.

16. The IED of claim 15, further comprising a second set of fNIRS optodes configured to capture second fNIRS signal data representing hemodynamic changes in the brain of the user, the second set of fNIRS optodes including:

at least one second source optode configured to transmit the light at one or more of the plurality of wavelengths into the head of the user along a second optical path; and a second detector optode configured to detect the light transmitted by the at least one second source optode, wherein the second optical path is reciprocal to the first optical path.

17. The IED of claim 16, wherein the controller is configured to generate the filtered fNIRS signal data by filtering the first fNIRS signal data based on the electrical signals and further based on the second fNIRS signal data.

18. The IED of claim 16, wherein the at least one first source optode and the second detector optode are disposed adjacent to each other at a first longitudinal end side of the IED, and wherein the first detector optode and the at least one second source optode are disposed adjacent to each other at a second longitudinal end side of the IED, and wherein a distance between the at least one first source optode and the first detector optode and a distance between the at least one second source optode and the second detector optode are more than a predetermined distance.

19. A method comprising:

capturing first fNIRS signal data with a first set of functional near-infrared spectroscopy (fNIRS) optodes disposed on an in-ear device (IED) configured to be placed within an ear canal of a user, the first fNIRS signal data representing hemodynamic changes in a brain of the user;

capturing electrical signals corresponding to brain activity of the user;

filtering the first fNIRS signal data based in part on the electrical signals to generate filtered fNIRS signal data;

using a machine-learned model to estimate an amount of blood oxygenation change in a superior temporal gyrus of the user based on the filtered fNIRS signal data, determining that the estimate of the amount of blood oxygenation change satisfies a threshold condition;

adjusting an audio setting of an audio signal of the IED based on the satisfaction of the threshold condition; and presenting the adjusted audio signal of the IED to the user.

20. The method of claim 19, further comprising capturing second fNIRS signal data with a second set of fNIRS optodes disposed on the IED, the second fNIRS signal data also representing hemodynamic changes in the brain of the user;

wherein the filtered fNIRS signal data is generated by filtering the first fNIRS signal data based on the electrical signals and further based on the second fNIRS signal data.

* * * * *